(12) United States Patent
Gunji et al.

(10) Patent No.: US 9,176,075 B2
(45) Date of Patent: Nov. 3, 2015

(54) CONTAMINATION INSPECTION METHOD AND CONTAMINATION INSPECTION DEVICE

(75) Inventors: Masanori Gunji, Hitachinaka (JP);
Tomonari Morioka, Hitachinaka (JP);
Hiroshi Akiyama, Hitachinaka (JP);
Hideki Fukushima, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 432 days.

(21) Appl. No.: 13/390,958

(22) PCT Filed: Jun. 21, 2010

(86) PCT No.: PCT/JP2010/004105
§ 371 (c)(1),
(2), (4) Date: Feb. 17, 2012

(87) PCT Pub. No.: WO2011/039910
PCT Pub. Date: Apr. 7, 2011

(65) Prior Publication Data
US 2012/0147364 A1 Jun. 14, 2012

(30) Foreign Application Priority Data

Sep. 30, 2009 (JP) ................................. 2009-225939

(51) Int. Cl.
*G01N 21/00* (2006.01)
*G01N 21/956* (2006.01)
*G01N 21/94* (2006.01)

(52) U.S. Cl.
CPC .......... *G01N 21/95623* (2013.01); *G01N 21/94* (2013.01)

(58) Field of Classification Search
CPC .............. G01N 21/9501; G01N 21/94; G01N 21/95623; G01N 21/956; G01N 21/9504; H01L 22/12; H01L 21/67288; G06K 9/2036
USPC ....................................................... 356/237.2
See application file for complete search history.

(56) References Cited

U.S. PATENT DOCUMENTS 5,107,351 A * 4/1992 Leib et al. ..................... 382/210
5,264,912 A * 11/1993 Vaught et al. ............... 356/237.5
(Continued)

FOREIGN PATENT DOCUMENTS

| JP | 10-068698 | 3/1998 |
| JP | 11-352075 | 12/1999 |

(Continued)

OTHER PUBLICATIONS

English translation for JP 2006-30215 (from applicant's IDS dated Feb. 17, 2012.*
Official Action issued in Japanese Patent Application No. 2013-035280 on Apr. 22, 2014.

*Primary Examiner* — Michael A Lyons
(74) *Attorney, Agent, or Firm* — Baker Botts L.L.P.

(57) ABSTRACT

Provided are a contamination inspection method and a contamination inspection device for highly accurately detecting a defect in a wafer, a liquid crystal substrate and media or the like including patterns, for example, a semiconductor device or the like. The first aspect of the present invention is a contamination inspection device comprising: an irradiation optical system for irradiating lights on the inspection target substrate; and a spatial filter for shading diffracted lights form the inspection target substrate. Herein, the spatial filter comprises: a plurality of light shading materials; a control member for changing at least one of parameters selected from a shape, an angle and an interval with respect to the light shading material, and a control unit for controlling the control members.

19 Claims, 29 Drawing Sheets

(56) References Cited

U.S. PATENT DOCUMENTS

| | | | |
|---|---|---|---|
| 5,463,459 A * | 10/1995 | Morioka et al. | 356/237.5 |
| 5,471,066 A * | 11/1995 | Hagiwara | 356/237.5 |
| 5,834,761 A * | 11/1998 | Okada et al. | 250/208.1 |
| 6,288,824 B1 * | 9/2001 | Kastalsky | 359/254 |
| 6,313,937 B1 * | 11/2001 | Dowe et al. | 359/280 |
| 7,184,138 B1 * | 2/2007 | Li | 356/237.2 |
| 2003/0132405 A1 * | 7/2003 | Some | 250/559.45 |
| 2005/0206887 A1 * | 9/2005 | Morioka et al. | 356/237.5 |

FOREIGN PATENT DOCUMENTS

| | | |
|---|---|---|
| JP | 2001-174629 | 6/2001 |
| JP | 2002-310932 | 10/2002 |
| JP | 2004-93333 | 3/2004 |
| JP | 2004-184142 | 7/2004 |
| JP | 2006-30215 | 2/2006 |
| JP | 2007-232555 | 9/2007 |

* cited by examiner

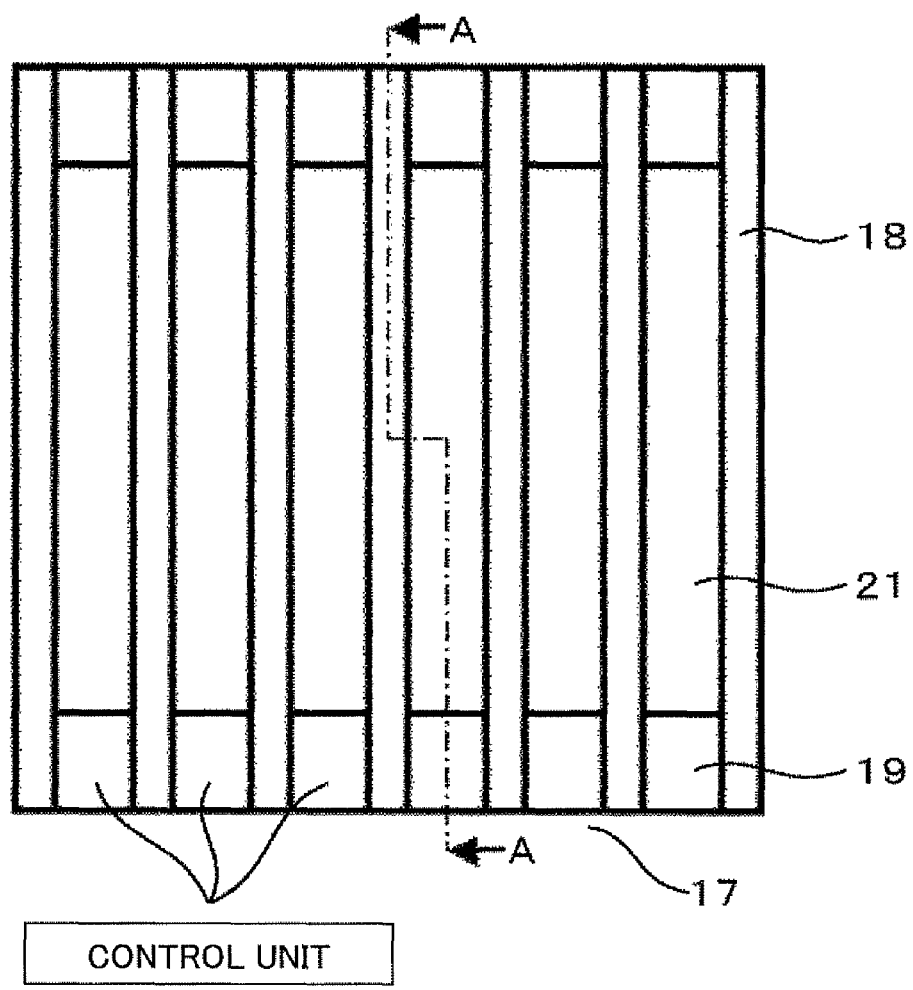

A-A CROSS SECTION

100: TENTATIVE REFERENCE AXIS

LIGHT DETECTION SIDE

REFLECTED LIGHT GENERATION SIDE

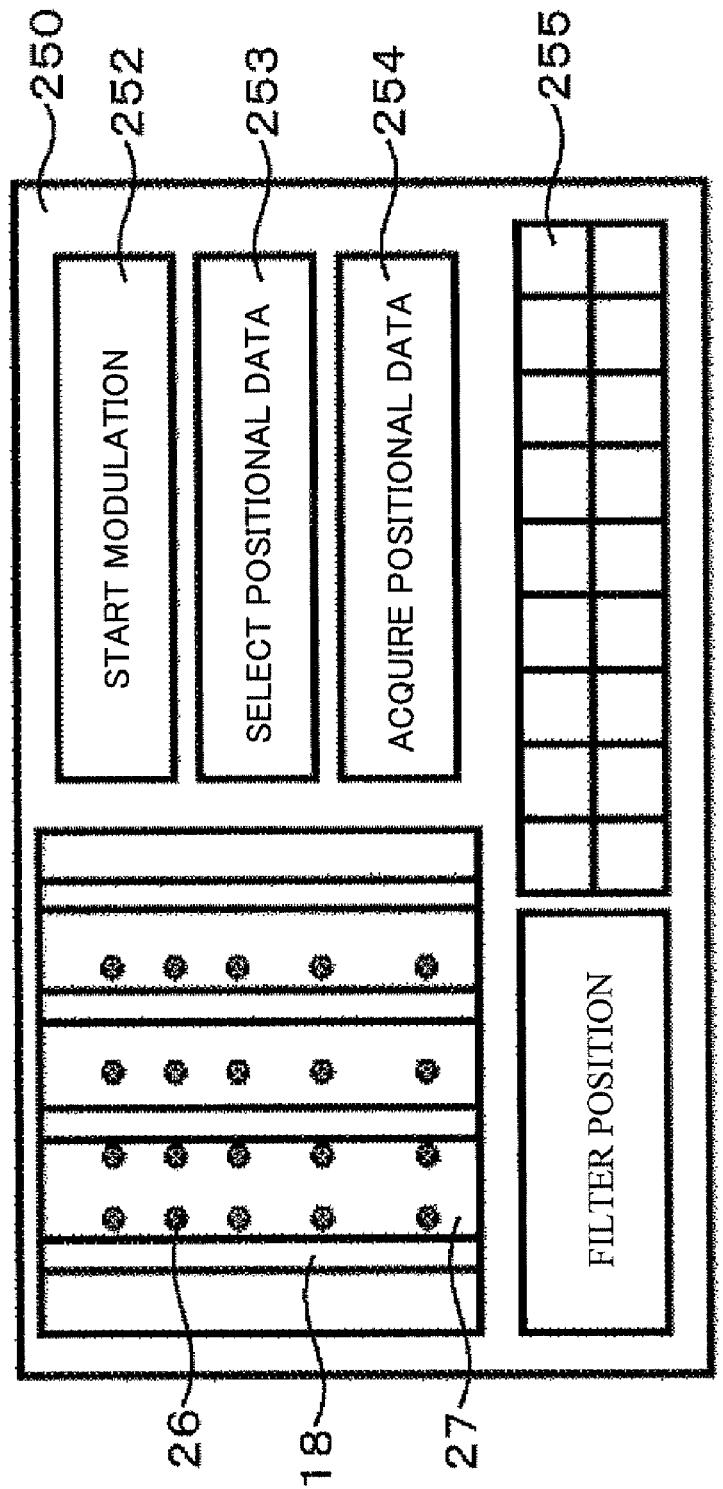

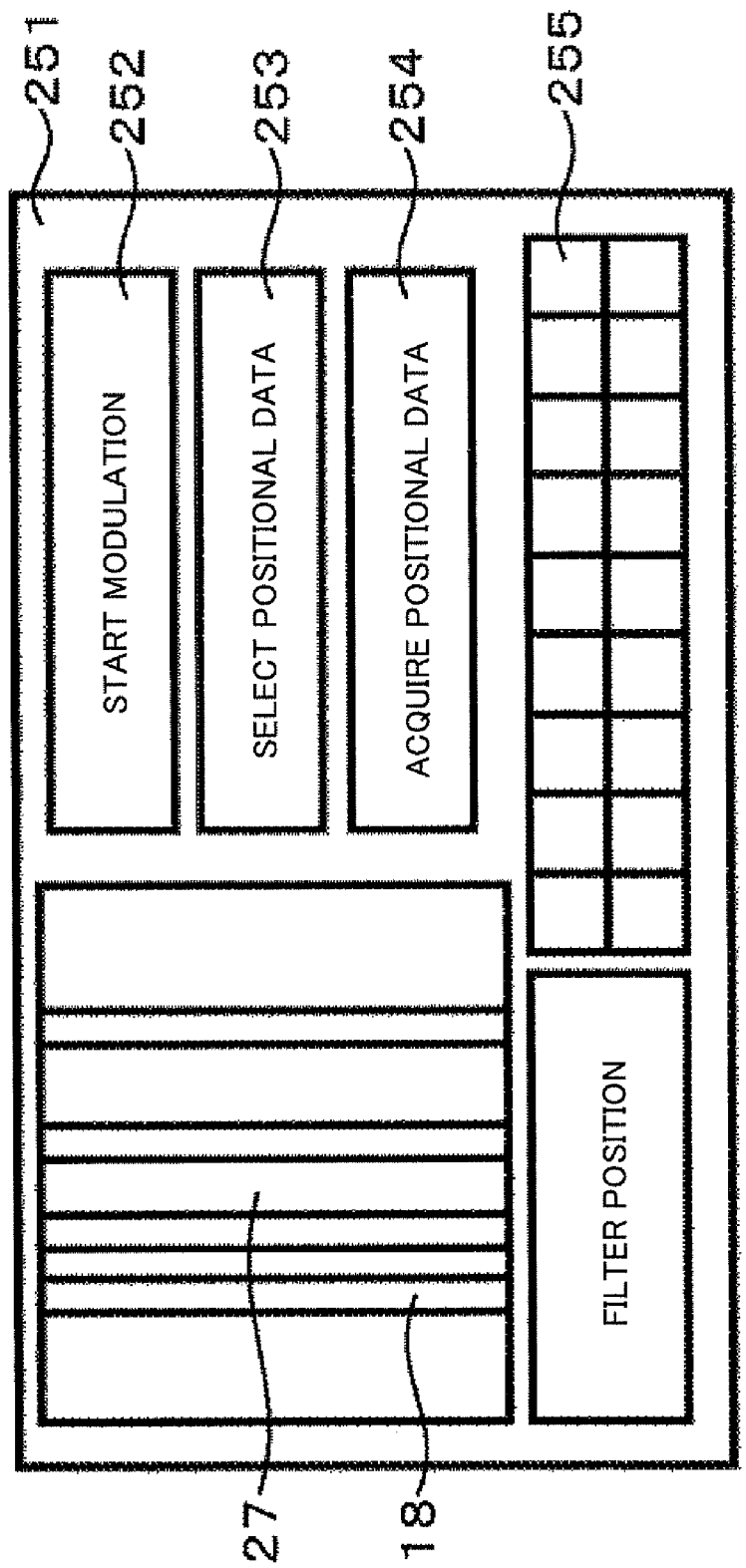

A-A CROSS SECTION

CONTROL UNIT

CONTROL UNIT

CONTAMINATION INSPECTION METHOD AND CONTAMINATION INSPECTION DEVICE

FIELD OF THE INVENTION

The present invention relates to a contamination inspection device and a contamination inspection method. More specifically, the present invention relates to a contamination inspection method and a device using the method, for inspecting defects and contaminations in a wafer, a liquid crystal substrate and media or the like comprising patterns, for example, a semiconductor device or the like.

BACKGROUND OF THE INVENTION

In a contamination inspection device, a spatial filter comprised of liquid crystal filters on which optional patterns are formed by picture elements consisting of dot matrices, forms a light shading pattern of diffracted lights projected on a Fourier transformation surface, by tuning on or off each picture element (that is, penetrating or shading lights). This may provide the light shading pattern formed by the spatial filter excellent in diversity of the pattern. However, incomplete light shading ability of a liquid crystal filter may cause malfunction allowing diffracted lights projected on a Fourier transformation surface, which must be essentially shaded, to penetrate the liquid crystal filters. In other words, this malfunction results in the lowering of the detecting accuracy. Therefore, in order to solve the above mentioned malfunction, a product improved with a shading rate thereof has been proposed, formed by stacking a plurality of liquid crystal filters. For example, Japanese Unexamined Patent Application Publication No. H11-352075 (or Patent Document 1) discloses the above mentioned invention.

Further, there is a mechanical spatial filter composed of light shading materials and coil springs, which is configured such that the light shading materials are joined to the coil springs. Such a mechanical spatial filter allows an interval between the light shading materials to be controlled and the light shading materials to be arranged at equal intervals through expanding or contracting the coil springs. Accordingly, the mechanical spatial filter is effective in an inspection target having a regular pattern. For example, Japanese Unexamined Patent Application Publication No. H10-68698 (or Patent Document 2) discloses the above mentioned invention.

PRIOR ART DOCUMENTS

Patent Literatures

[Patent Document 1] Japanese Unexamined Patent Application Publication No. H11-352075
[Patent Document 2] Japanese Unexamined Patent Application Publication No. H10-68698

DISCLOSURE OF THE INVENTION

Problems to be Solved by the Invention

The liquid crystal filter is comprised of pixels each having a several tens μm size. Accordingly, such a liquid crystal filter fails to form and arrange the light shading pattern against the diffracted lights projected on the Fourier transformation surface with high accuracy. This results in the failure in highly resolutional filtering. Further, the diffracted lights projected on the Fourier transformation surface penetrate a lens, which causes distortion due to a lens aberration. Hereby, extremely small lens aberration is unable to be corrected with respect to the light shading pattern formed by the liquid crystal filters, leading to a drawback in detecting a contamination signal with high accuracy.

Here, the diffracted lights, projected on a Fourier transformation surface from a part having a repeated pattern such as a memory cell pattern represented by a DRAM (Dynamic Random Access Memory), are projected having a wide pitch, while the diffracted lights, projected from a part having a less repeated pattern such as a peripheral portion of a DRAM, are projected having a narrow pitch or a continuous distribution. Accordingly, the diffracted lights having different intervals are projected on the Fourier transformation surface. Hereby, since the mechanical filter has a structure that the light shading materials are joined to the coil springs at equal intervals, the mechanical filter is unable to control the positioning of the extremely small shading material, thereby to fall in the failure in corresponding to the light shading patterns having different intervals projected on the Fourier transformation surface. Herein, the drawback may be solved by assuming a spatial filter which arranges light shading materials joined to coil springs at uneven intervals. However, a number of spatial filters have to be prepared in order to correspond to the various light shading patterns, resulting in the increase in the cost and size of the spatial filter unit. Therefore, the above mentioned solution is not realistic.

Accordingly, an object of the present invention is to provide a contamination inspection method and a contamination inspection device, having high accuracy.

Further, another object of the present invention is to provide light shading patterns formed by various spatial filters.

Means for Solving the Problems

A first aspect of the present invention is to provide a contamination inspection device comprising: an irradiation optical system for irradiating lights to an inspection target substrate; a detecting optical system for detecting the lights from the inspection target substrate; and a spatial filter for shading the diffracted lights from the inspection target substrate. Herein, the spatial filter comprises: a plurality of light shading materials; a control member for changing at least one of the parameters selected from a shape, an angle, and an interval with respect to the light shading material; and a control unit for controlling the control member.

A second aspect of the present invention is that the control unit controls at least one of the parameters selected from a voltage, a magnetic field, and a flow rate of fluid, applied to the control member.

A third aspect of the present invention is that the control member is comprised of a piezoelectric member.

A fourth aspect of the present invention is that the control member is comprised of an elastic material.

A fifth aspect of the present invention is that the control member is comprised of at least two rotational members connected with the light shading materials.

A sixth aspect of the present invention is that the light shading material is constituted of at least two or more members. Herein, one of the members is a piezoelectric material, and the other is a voltage control unit which applies a voltage to the piezoelectric material.

A seventh aspect of the present invention is that the control member is comprised of motors arranged at both ends of the light shading material.

An eighth aspect of the present invention is that the control member comprises a magnetic substance.

A ninth aspect of the present invention is shading of the diffracted lights by using at least one of the members selected from a piezoelectric effect, fluid, magnetic force, and electrostatic force.

Advantageous Effects of the Invention

Next, will be briefly explained representative effects achieved by the present invention, disclosed in the specification as follows:

(1) A contamination inspection method and a contamination inspection device, with high accuracy may be provided.

(2) Light shading patterns by using various spatial filters may be provided.

BRIEF DESCRIPTION OF THE DRAWINGS

FIGS. 1A and 1B are explanatory diagrams showing a spatial filter in the first embodiment of the present invention.

FIGS. 7A and 7B are GUI screens when the spatial filter in the first embodiment of the present invention is modulated.

BEST MODE FOR CARRYING OUT THE INVENTION

Hereinafter, embodiments of the present invention will be explained in detail, referring to the attached drawings. However, the present invention is not limited to these embodiments and various modifications may be performed.

[First Embodiment]

Figure 2:
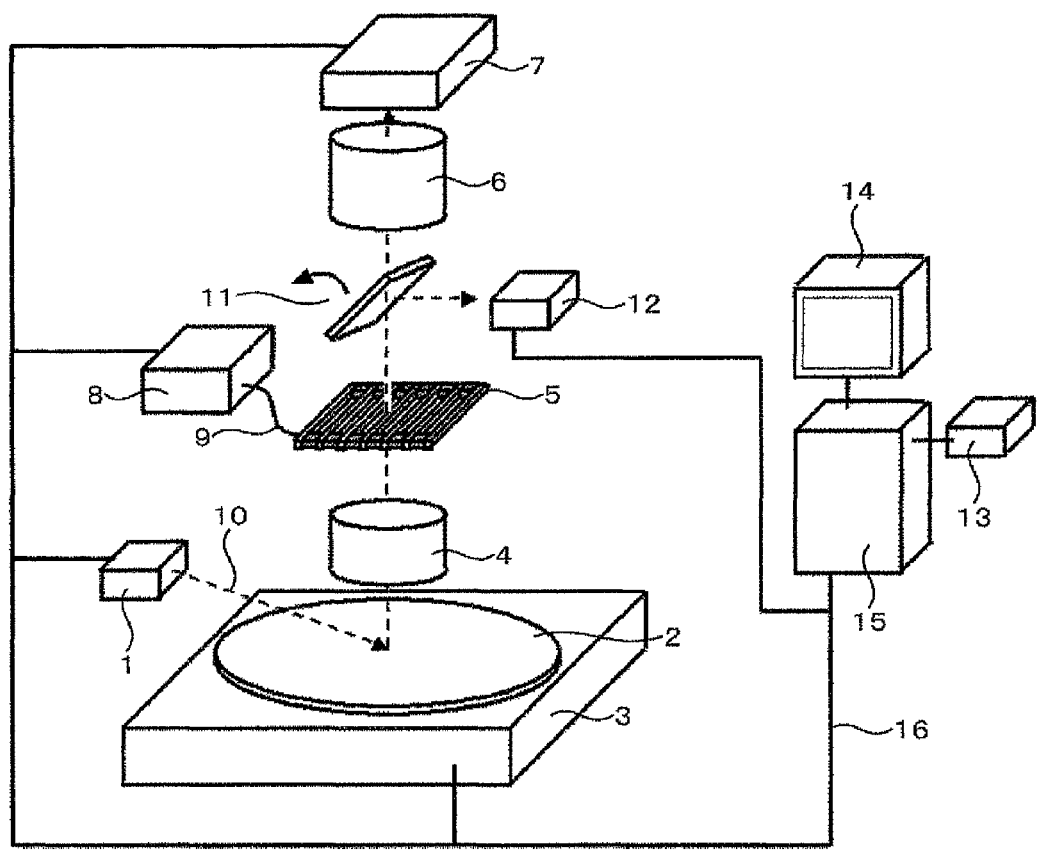
FIG. 2 is a schematic diagram showing a construction of the contamination inspection device.

FIG. 2 shows a whole construction of a contamination inspection device of the first embodiment.

The contamination inspection device in the first embodiment comprises a laser 1 and a stage 3, and is configured to have a detection lens 4, a spatial filter 5, a spatial filter control unit 8, a spatial filter controlling cable 9, a half mirror 11, a CCD (Charge Coupled Device) camera 12, a condensing lens system 6, a detector 7, a keyboard for inputting data and operating devices 13, a monitor 14, a control personal computer 15, and a control and data collecting cable 16. A wafer 2 is held on the stage 3 and a laser beam 10 is irradiated from a laser 1 on a surface of the wafer 2, thereby to scan the wafer 2 by moving the stage 3 in the x and y directions (or two dimensional motion).

When the laser beam 10 is irradiated, diffracted lights are generated by the devices and wiring formed on the substrate, while scattered lights are generated if a contamination is attached to the wafer 2. Since the diffracted lights are projected on the Fourier transformation surface, it is possible to obtain the image data on the diffracted lights projected on the Fourier transformation surface and the state of the spatial filter through the half mirror 11 and the CCD camera 12, allowing the image to be displayed on the monitor 14. Herein, if the half mirror 11 influences attenuation of the diffracted lights and scattered lights, a mechanism of moving the half mirror 11 apart from the optical axis maybe utilized. Further, note an angle of positioning the spatial filter 5 is not specifically defined here. That is because angles of the diffracted lights projected on the Fourier transformation surface are changed by the position of the laser 1. Hereby, the spatial filter 5 maybe equipped with a rotation mechanism, so as to modulate the angle of the spatial filter 5.

Further, the spatial filter 5 may be controlled to obtain an optimal light shading pattern while monitoring by the CCD camera 12 the light shading state of the diffracted lights projected on the Fourier transformation surface. However, generally the spatial filter 5 is controlled to obtain the light shading pattern determined in advance by simulations based on the measurement data in the past or the design data. Those steps enable the diffracted lights to be efficiently removed by the spatial filter 5, and the images of the devices and wiring regularly formed on the substrate to be removed from the images taken by the detector 7, resulting in a proceeding of the appropriate contamination inspection.

Figure 1B:
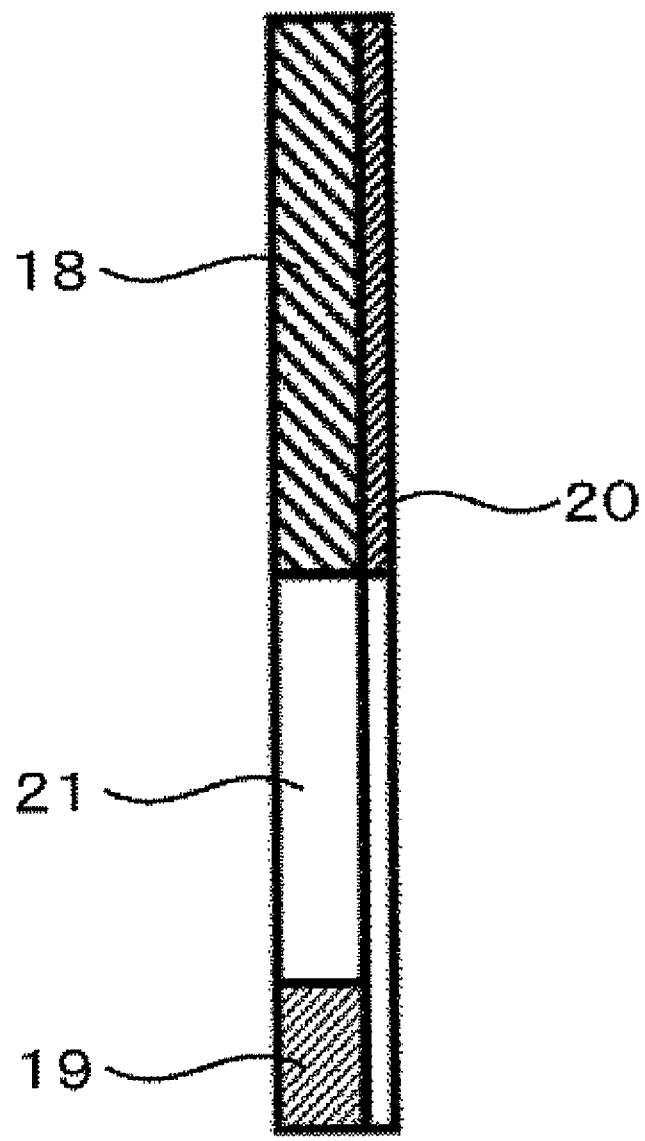

Next, will be explained a spatial filter 17 of the present invention. FIGS. 1A and 1B show the spatial filter in the first embodiment. Herein, FIG. 1A shows a top view and FIG. 2b shows a cross-sectional view of the spatial filter 17.

The spatial filter 17 comprises a light shading material 18, a piezoelectric element 19, an anti-reflection material 20 and a control unit. The anti-reflection material 20 is formed on a surface of the rod-shaped light shading material 18 (or a surface facing to the detection lens 4). The light shading material 18 and the adjacent light shading material 18 are adhesively held through the piezoelectric elements 19. The respective piezoelectric elements 19 are independently connected to the control unit (not shown the all of the wiring).

Figure 3A:
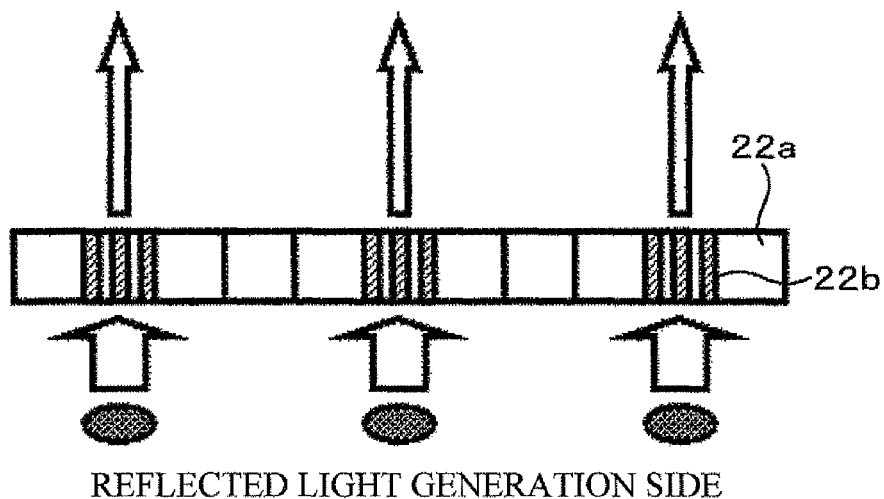
FIGS. 3A and 3B are explanatory diagrams showing a light shading method for using a conventional spatial filter (or liquid crystal filter).
Figure 3B:
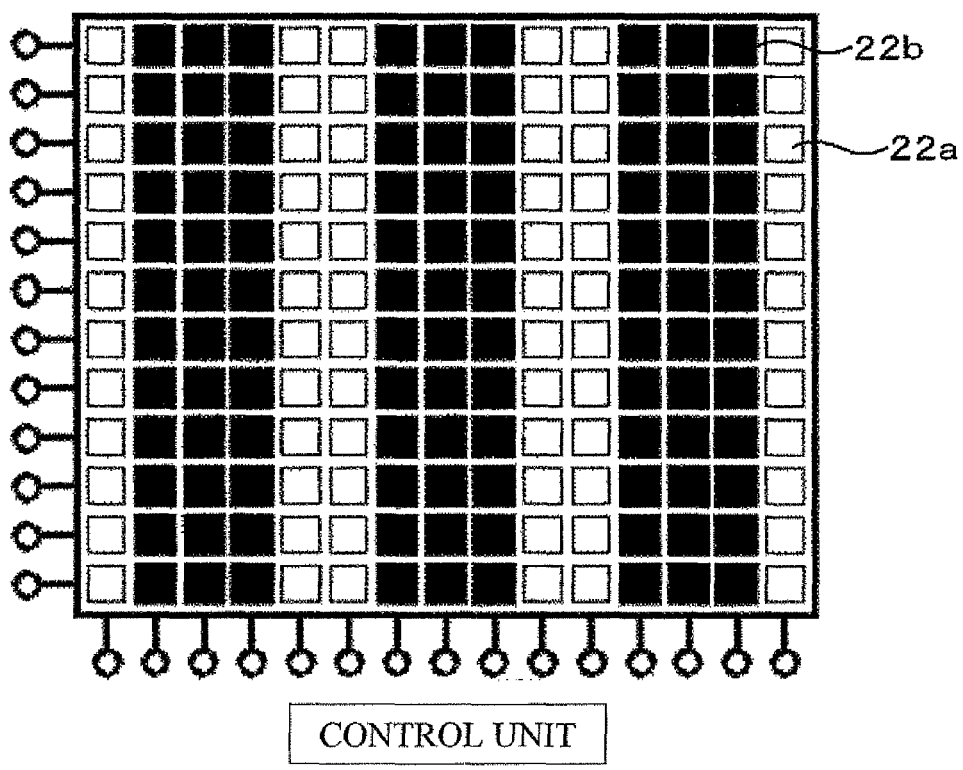

Next, will be explained a feature of the spatial filter 17 of the present invention. FIGS. 3A, 3B, 4A and 4B show conventional spatial filters. FIGS. 3A and 3B indicate liquid crystal filters, while FIGS. 4A and 4B indicate coil spring type of mechanical filters. In FIGS. 3A and 3B, the spatial filter is comprised of picture elements made of liquid crystal filters arranged in dot matrix-like. Herein, the light shading rate is not 100% due to generation of a gap between the picture elements, allowing the diffracted lights which should be shaded to penetrate the spatial filter and to be projected on the Fourier transformation surface.

Figure 4A:
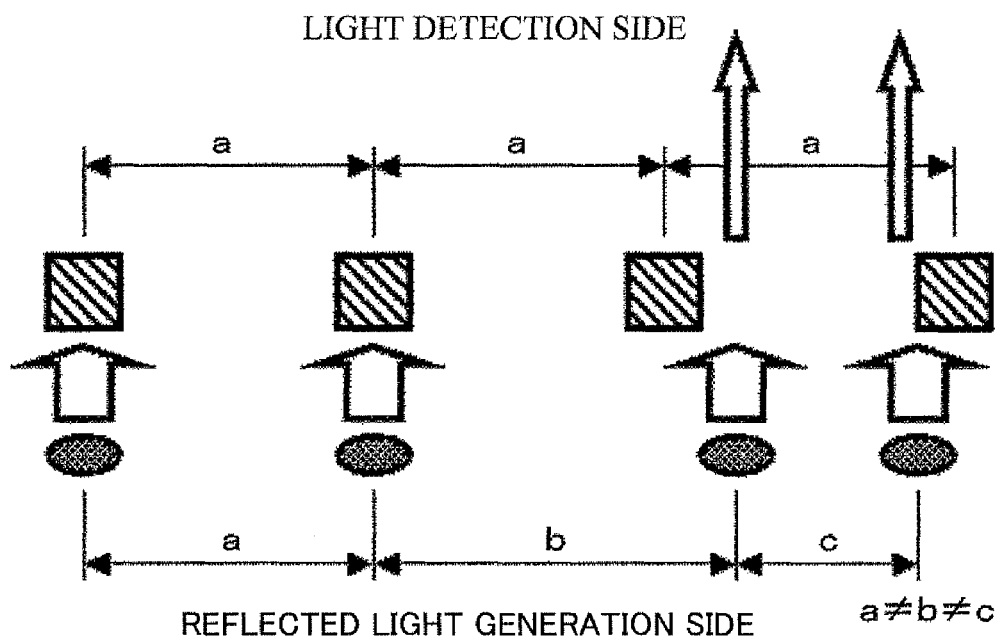
FIGS. 4A and 4B are explanatory diagrams showing a light shading method for using a conventional spatial filter (or coil spring type of mechanical filter).
Figure 4B:
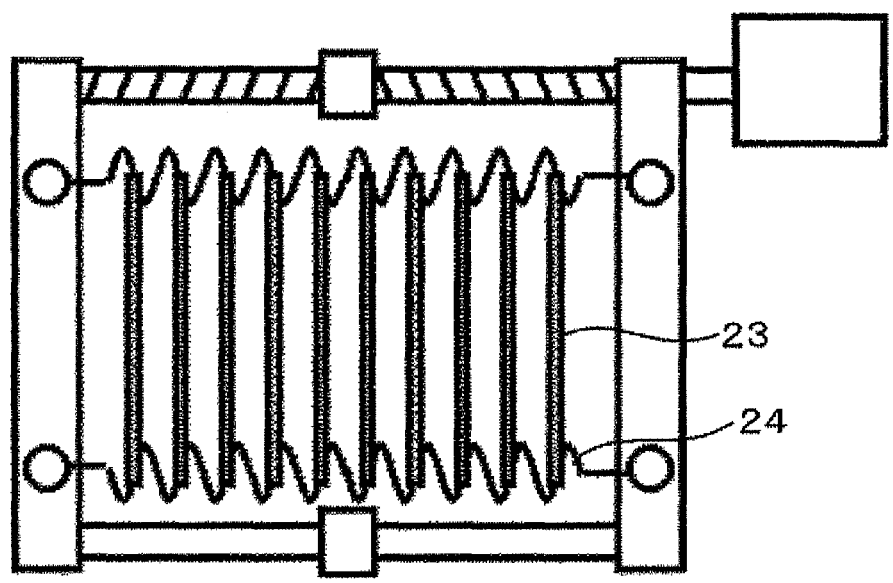

In FIGS. 4A and 4B, the light shading materials 23 are adhesively held to the coil springs 24 at equal intervals. This prevents the intervals between the adjacent light shading materials from being changed to uneven intervals, instead, only keeping the equal intervals, even though making the coil springs 24 expanded or contracted. That is, this leads to the lowering of the detection accuracy.

Figure 5A:
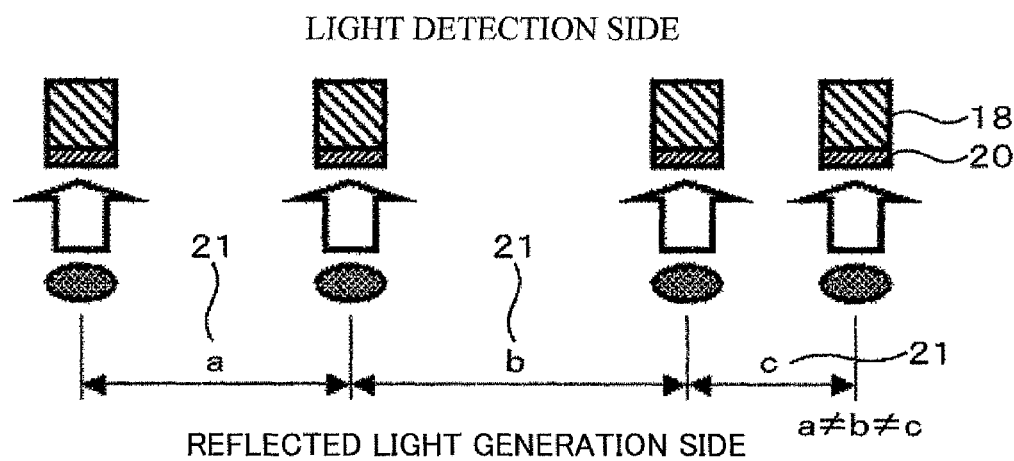
FIGS. 5A and 5B are explanatory diagrams showing a light shading method for using a spatial filter in the first embodiment of the present invention.
Figure 5B:
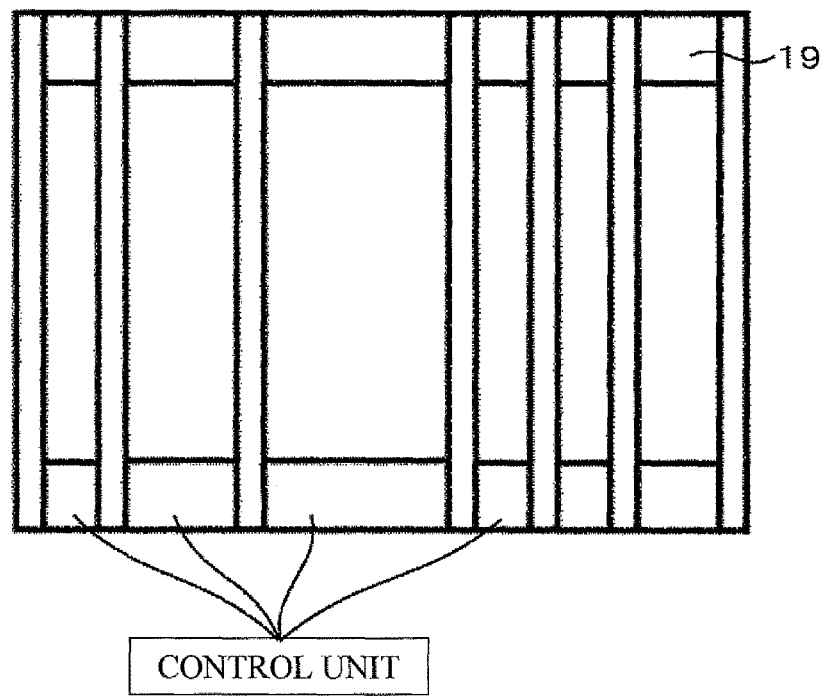

As shown in FIGS. 5A and 5B, in order to solve the above mentioned malfunction, the light shading materials 18, which are made by applying an anti-reflection material 20 to stainless steel materials, are utilized in the present invention. This allows the diffracted lights projected on the Fourier transformation surface to be shaded in 100%. Further, the piezoelectric element 19 of which expansion and contraction are proportional to the applied voltage is used, and each piezoelectric element 19 is configured to be independently connected with the control unit. This construction allows each interval between the adjacent light shading materials 21 to be modulated at an equal interval or at an uneven interval by independently controlling the applied voltage to each piezoelectric element 19.

Figure 1C:
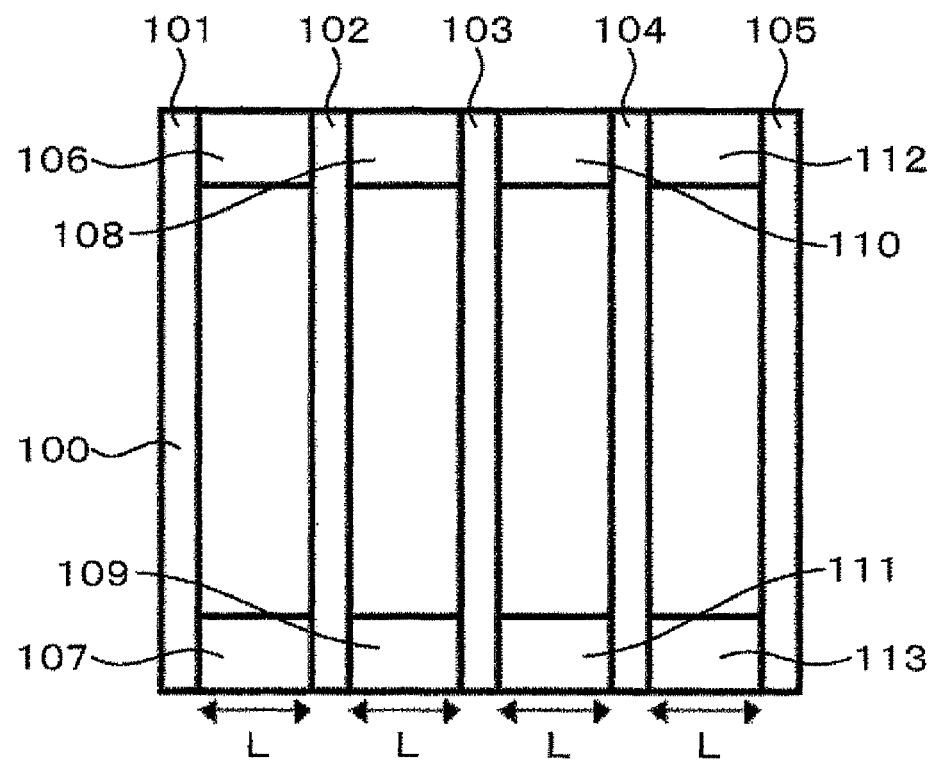
FIGS. 1C and 1D are explanatory diagrams showing a case in changing intervals between light shading materials and angles thereof.
Figure 1D:
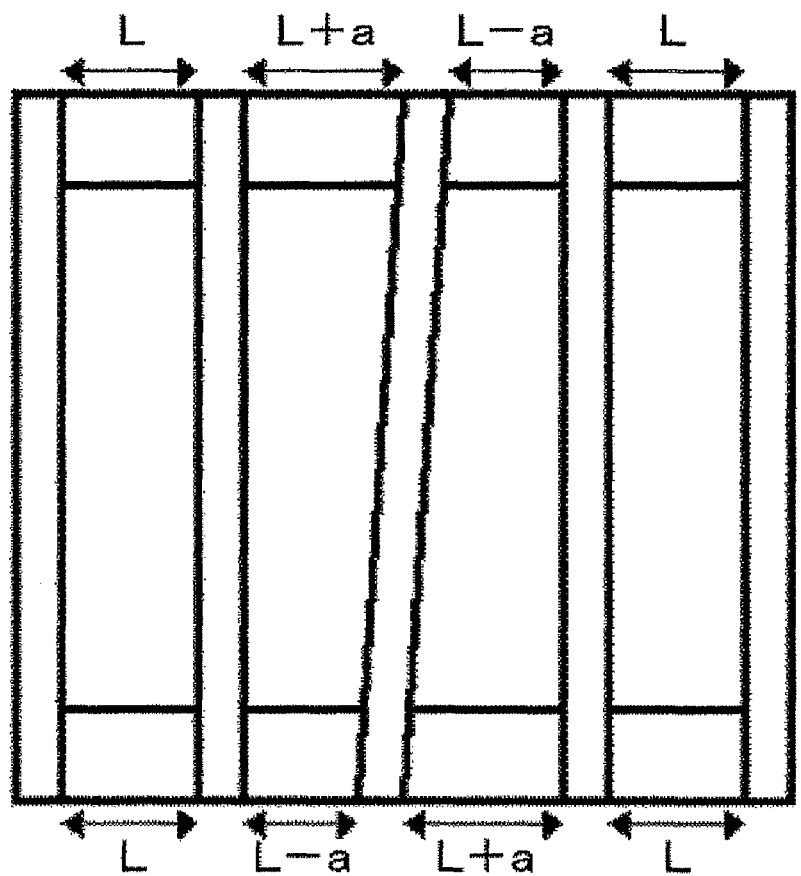

When the applied voltage to the piezoelectric element 19 is increased, the piezoelectric element 19 is extended, and the piezoelectric element 19 is contracted when the applied voltage to the piezoelectric element 19 is decreased. For example, as shown in FIG. 1C, 50% of the maximum applied voltage is applied to the piezoelectric elements 106 to 113, and thereby the light shading materials 101 to 105 are arranged at equal intervals. Then, 20% of the maximum applied voltage further applied to the piezoelectric elements 108 and 111, while 20% of the maximum applied voltage is decreased and the less voltage is applied to the piezoelectric elements 109 and 110. Accordingly, only the light shading material 103 may be controlled as shown in FIG. 1D. This enables the light shading material 103 to be arranged inclined with a certain angle against the other light shading materials.

Figure 1E:
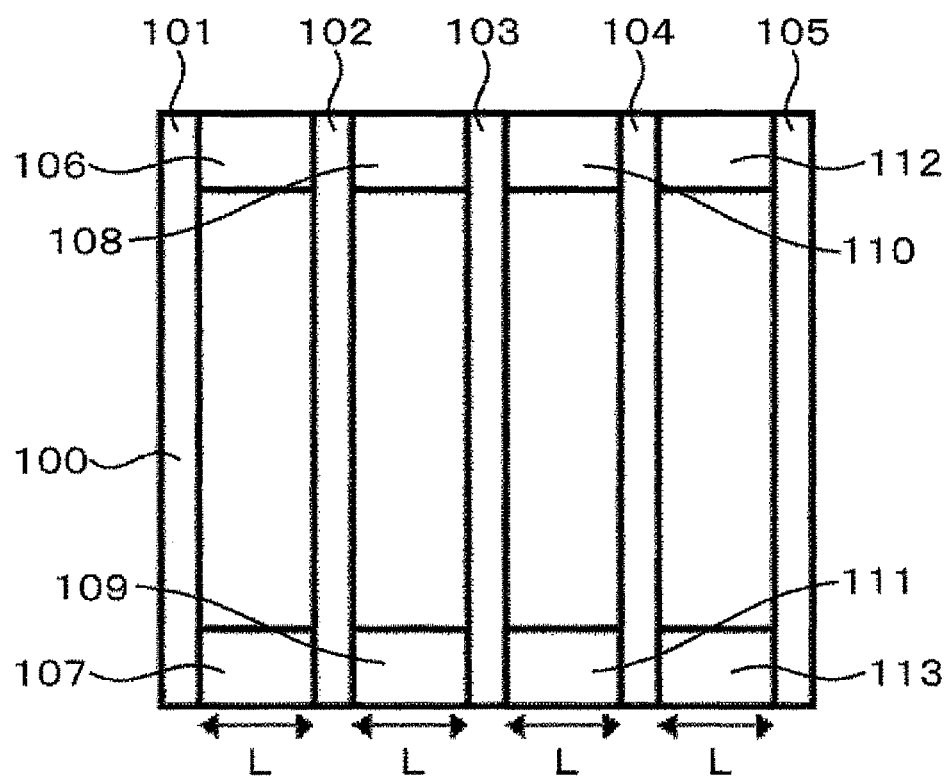
FIGS. 1E and 1F are explanatory diagrams showing a case in independently changing respective intervals between the light shading materials.
Figure 1F:
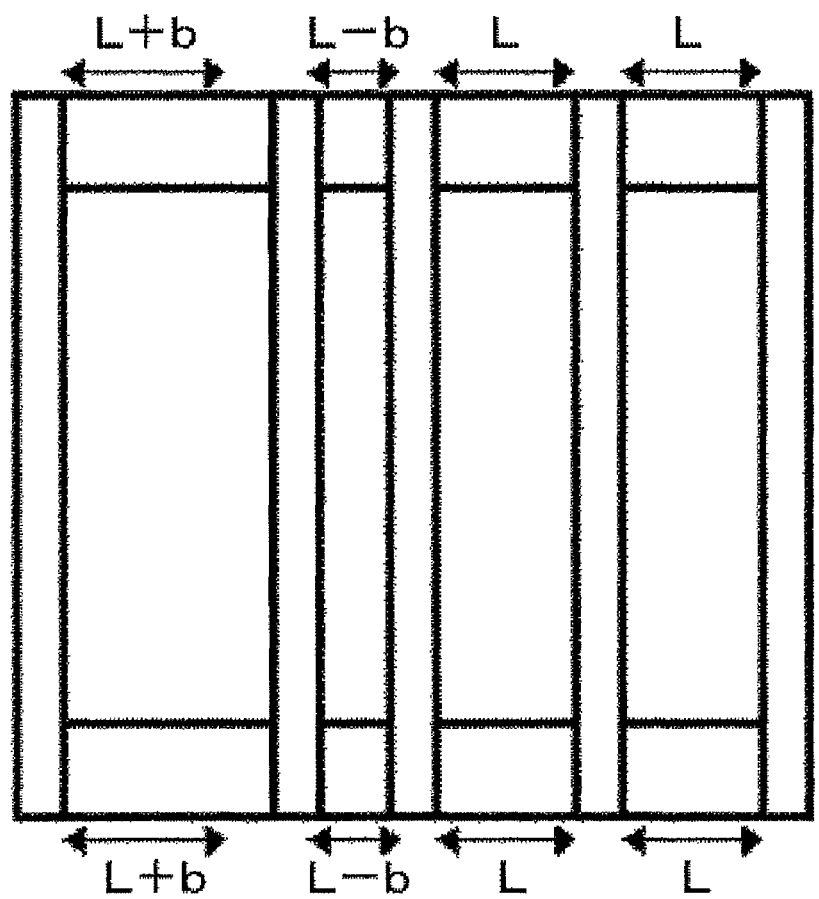

Next, as shown in FIG. 1E, 50% of the maximum applied voltage is applied to the piezoelectric elements 106 and 113. Then, 30% of the maximum applied voltage is further added to the piezoelectric elements 106 and 107, while 30% of the maximum applied voltage is decreased and the less voltage is applied to the piezoelectric elements 108 and 109. Accordingly, this enables only the light shading material 102 to be controlled, thereby to arrange the light shading materials in parallel and at uneven intervals, as shown in FIG. 1F.

Figure 1G:
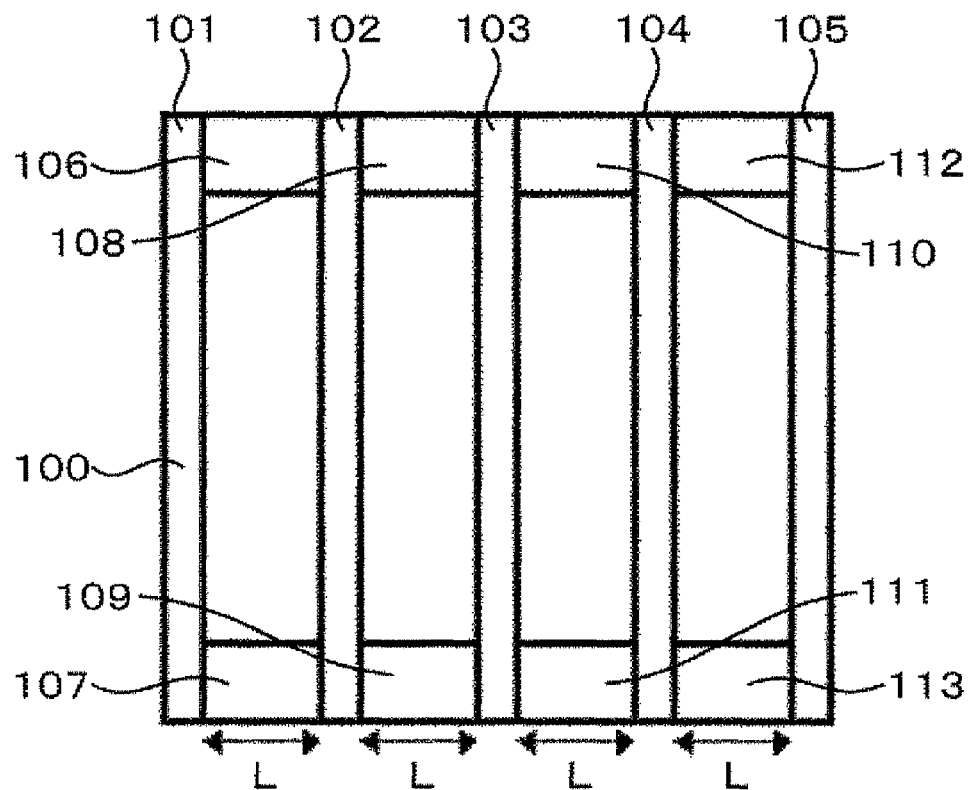
FIGS. 1G and 1H are explanatory diagrams showing a case in arranging the intervals of the light shading materials at equal intervals, while inclining the light shading materials 102-105 against the light shading material 101 with a certain angle.
Figure 1H:
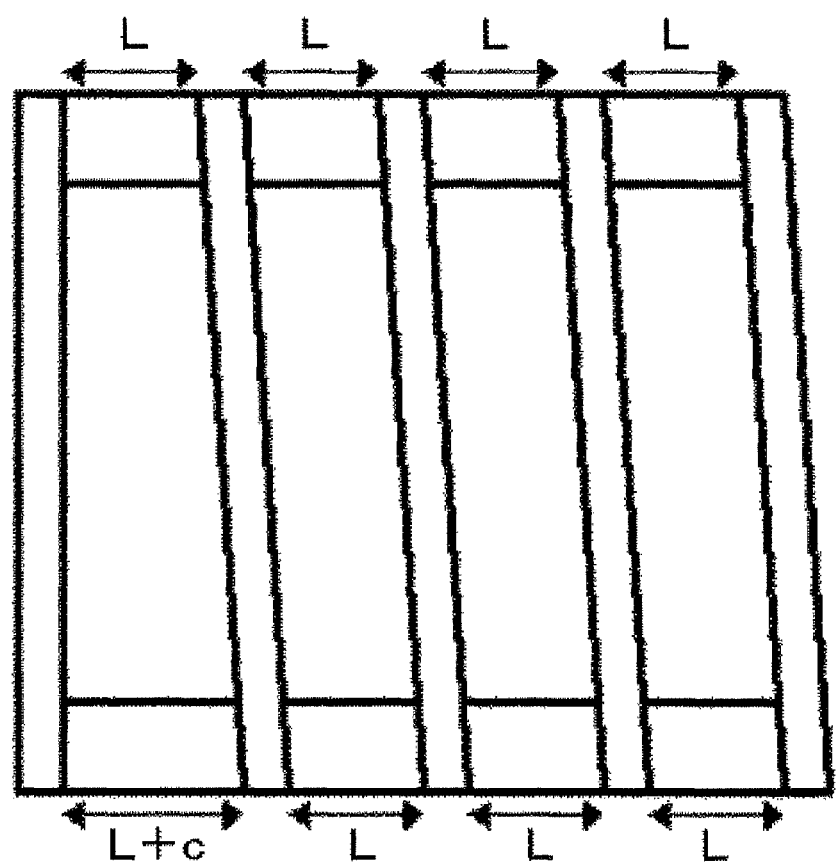

Further, as shown in FIG. 1G, 50% of the maximum applied voltage is applied to the piezoelectric elements 106 and 113. Then, 25% of the maximum applied voltage is further added to the piezoelectric element 107, which allows the light shading materials 102 to 105 to be arranged at equal intervals and inclined with a certain angle against the light shading material 101 as shown in FIG. 1H.

Figure 1I:
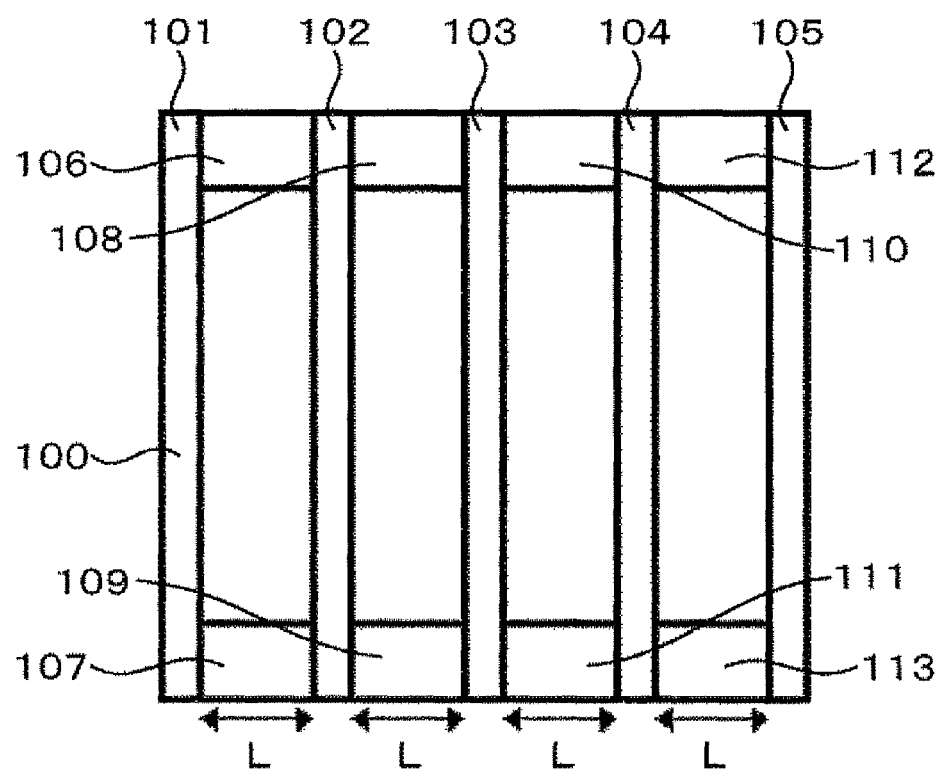
FIGS. 1I and 1J are explanatory diagrams showing a case in inclining the light shading materials 101 and 102 therebetween with a certain angle, while inclining the light shading materials 102 and 103 therebetween with a different angle.
Figure 1J:
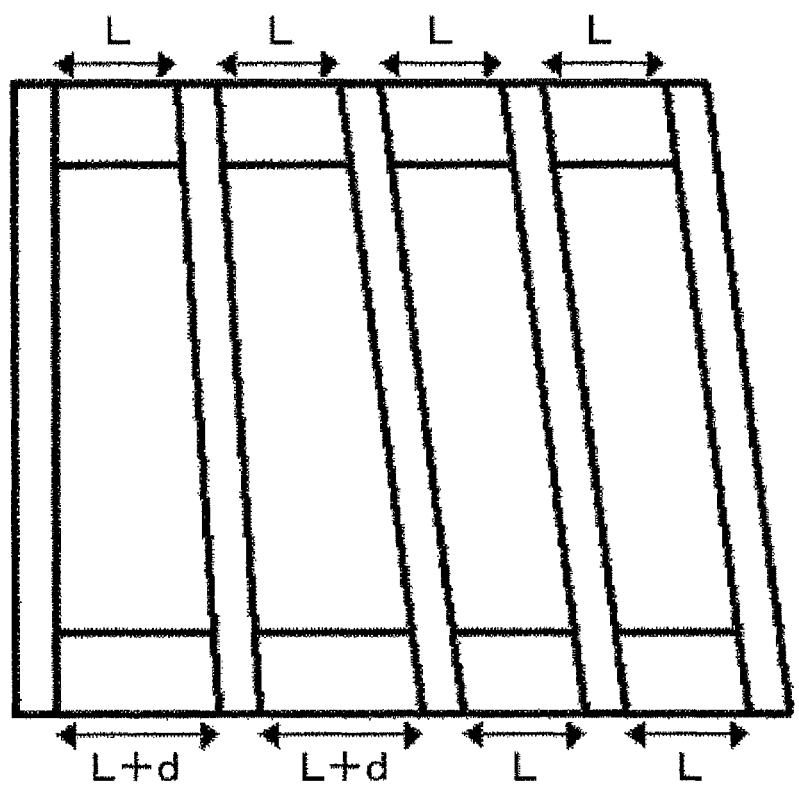

Moreover, as shown in FIG. 1I, 50% of the maximum applied voltage is applied to the piezoelectric elements 106 and 113. Then, 35% of the maximum applied voltage is further added to the piezoelectric elements 107 and 109, which enables the arrangement in which an angle between the light shading materials 101 and 102 and an angle between the light shading materials 102 and 103 are different, as shown in FIG. 1J.

As mentioned hereinbefore, the modification of the applied voltage to the individual piezoelectric element allows the arrangement of each light shading material to be changed.

Figure 6A:
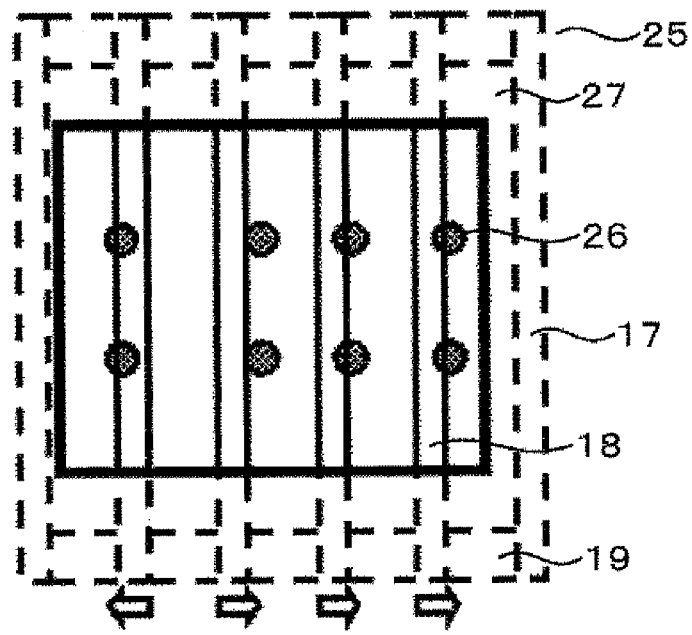
FIGS. 6A and 6B are explanatory diagrams showing the inspection images formed by the spatial filter in the first embodiment of the present invention.

Hereinafter, a specific inspection procedure will be explained. FIG. 6A shows an inspection image displayed on a screen of the monitor 14, indicating diffracted lights 26 projected on the Fourier transformation surface, and the light shading materials 18 of the spatial filter 17, taken by the CCD camera 12. The inspection procedure comprises the steps of: first displaying an image of the diffracted lights 26 projected on the Fourier transformation surface on an inspection screen 25; and secondly displaying the spatial filter 17 on the inspection screen 25 (referring to FIG. 6A).

Figure 6B:
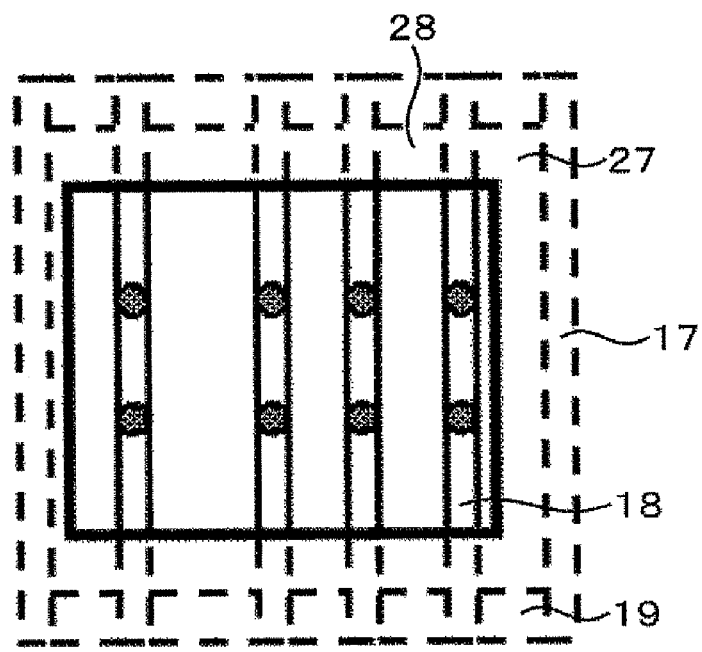

Next, expansion and contraction of the piezoelectric elements 19 move light shading materials 18, and this movement has the respective light shading materials 18 overlap the diffracted lights 26 projected on the Fourier transformation surface (referring to FIG. 6B).

Next, FIGS. 7A and 7B show modulation screens 250: GUI (Graphic User Interface) when a light shading interval 27 between the light shading materials 18 in the spatial filter 17 is modulated. The positions of the light shading materials may be controlled by modulating the light shading pattern of the spatial filter 17, thereby to be operated through the modulation screen 250 (referring to FIG. 7A). FIG. 7B shows a modulation screen 251 displaying that the modulation of the spatial filter 25 has completed, whereby the light shielding materials 18 overlap the diffracted lights 26 projected on the Fourier transformation surface.

Figure 8:
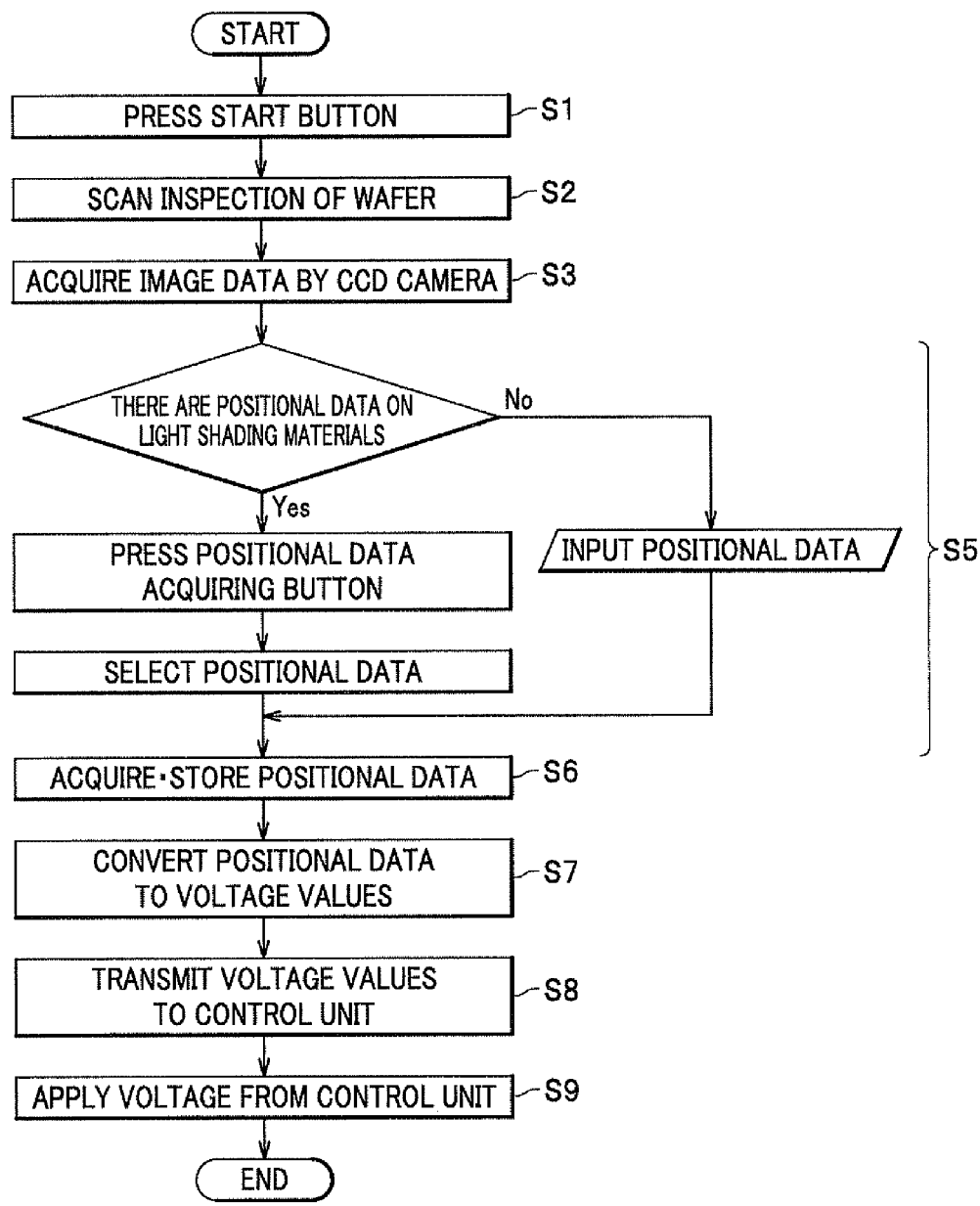
FIG. 8 is a flowchart when the spatial filter in the first embodiment of the present invention is modulated.

FIG. 8 shows a flowchart for controlling the piezoelectric elements. When a modulation start button 252 displayed on a GUI screen of a modulation screen 250 is pressed, is started a step of modulating the light shading material interval 27 between the adjacent light shading materials 18 in the spatial filter 17 (step S1). Then, a laser beam 10 is irradiated from a laser 1 to inspectionally scan a wafer 2 (step S2). Image data are acquired through a CCD camera 12 (step S3) and the image data are displayed on a monitor 14 as show on the modulation screen 250. If positional data on the light shading materials 18 and positional data on the light shading material interval 28 are already stored, a positional data selection button 253 is pressed to select a file including the positional data. However, if no positional data are stored, the corresponding positional data are inputted into a positional data input field 255 (step S5).

When the positional data are selected, a positional data acquiring button 254 is pressed, thereby to acquire the positional data and store the file thereof (step S6). Since the positional data cannot be directly used for the control unit of the piezoelectric elements 19, the positional data are converted to voltage value data (step S7). The converted voltage value data are transmitted to the spatial filter control unit 8 through the control and data acquiring cable 16 (step S8). The spatial filter control unit 8 applies voltages to the piezoelectric elements 19 through the spatial filter control cable 9 based on the received voltage value data (step S9).

The above mentioned steps allow the positions of the light shading materials 18 in the spatial filter 17 to be controlled, resulting in the achievement of modulating the light shading pattern.

Here, it should be noted that a method for acquiring the positional data by the step that the strength of the diffracted lights becomes minimum may be utilized, or another method for acquiring the positional data by conducting simulation based on the design data on a semiconductor device.

Further, has been explained a case that the modulation screen 205 displays one spatial filter 17, while the positional control of the light shading filters 18 may be also performed in the same steps as described hereinbefore, even when there are two detectors 7 or when two or more spatial filters 17 are arranged in the same detection system. Moreover, the light shading materials 18 of the spatial filter 17 are displayed vertically on the modulation screen 250. However, the light shading materials 18 may be displayed as having an inclining angle, for example, of 45 degrees on the modulation screen 250.

As mentioned above, the light shading material interval 27 maybe freely changed to be equal to or an uneven with respect to the adjacent light shading material interval 28. Accordingly this allows a highly accurate contamination inspection to be realized.

Note an aspect ratio of the inspection image shown in FIGS. 7A and 7B is not even, while the aspect ratio may be even. Further, the piezoelectric elements 19 are displayed outside the inspection screen, while the piezoelectric elements 19 may be displayed inside the screen. Further, the order of displaying the light shading pattern and the spatial filter 17 on the inspection screen may be opposite to the present embodiment, or at the same time. Moreover, the present embodiment shows a case that the diffracted lights 26 projected on the Fourier transformation surface have uneven intervals, while the diffracted lights 26 may have equal intervals. Furthermore, in the present embodiment, the piezoelectric elements 19 driven by applying voltage thereto are utilized. Herein, the driving source may include electrostatic force, heat, and magnetic force or the like.

Further, the anti-reflection material may be applied to not only a lens 4 side of the light shading material but both sides of the light shading material or the whole surface thereof.

[Second Embodiment]

Figure 9:
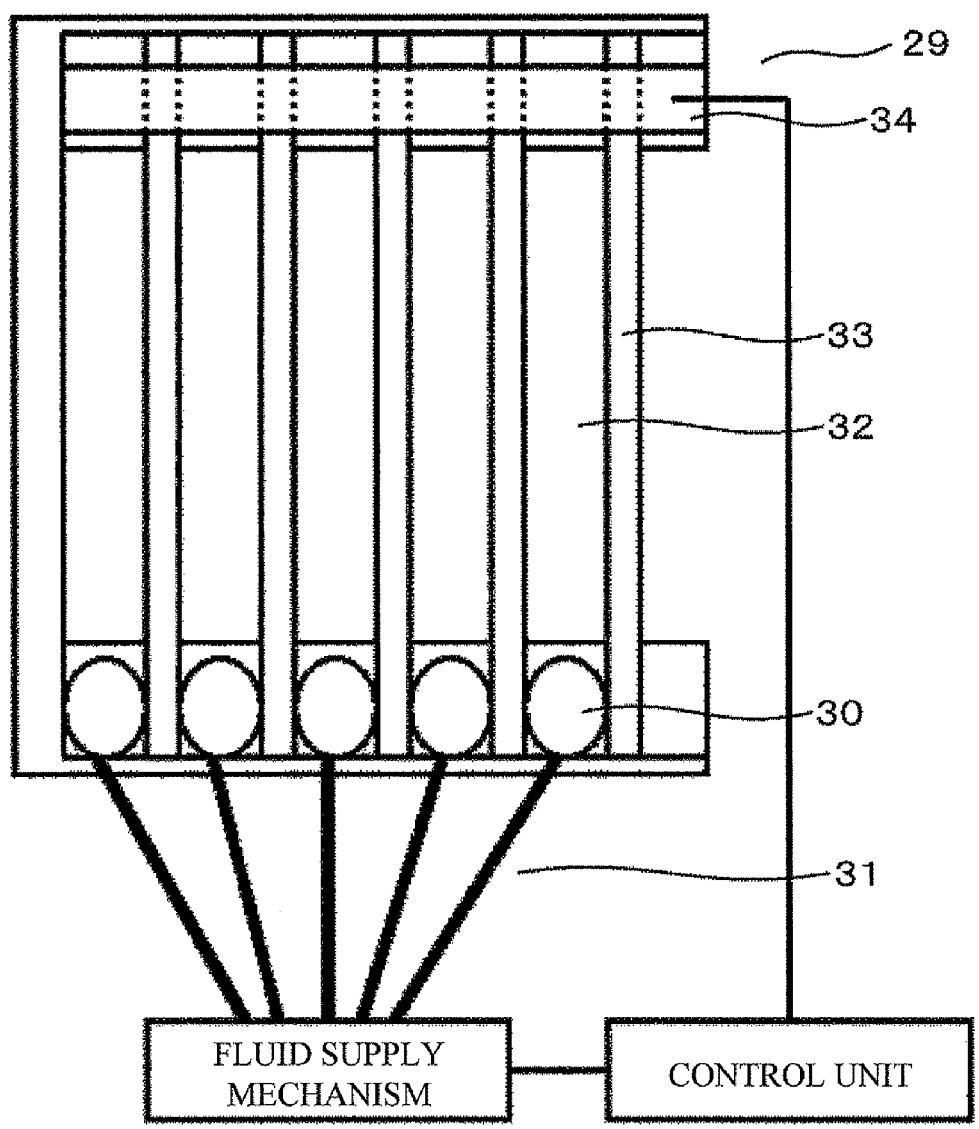
FIG. 9 is an explanatory diagram of a spatial filter in the second embodiment of the present invention.

Next, referring to FIG. 9, will be explained the second embodiment of the present invention.

When the spatial filter 29 in the second embodiment is compared to the spatial filter 17 in the first embodiment, there is a difference that elastic materials driven by fluid 30 are included instead of the piezoelectric elements 19. The respective elastic materials driven by fluid 30 are independently connected with a fluid supply mechanism through tubes 31. The respective light shading material intervals 32 may be independently controlled by supplying the fluid from the fluid supply mechanism to the respective elastic materials driven by fluid 30, or conversely by sucking the fluid from the respective elastic materials driven by fluid 30 to the fluid supply mechanism.

The supply or suck of the fluid to or from the respective elastic materials driven by fluid 30 enables the respective elastic materials driven by fluid 30 to be expanded or contracted, which allows the light shading materials 33 to be moved. In FIG. 9, the fluid supply mechanism is arranged at only one side of the light shading materials 33, and the light shading materials 33 only move in parallel shifts. Alternatively, the respective elastic materials driven by fluid 30 connected with the fluid supply mechanism may be arranged at both sides of the light shading materials 33 (That is, at the upper side and the lower side in FIG. 9). For example, the expansion or contraction length of an elastic body arranged at each side may be changed, for example, one length being X mm and the other length being 2×mm. This procedure allows the light shading materials 33 to be arranged with inclining angles same as in the first embodiment.

In the first embodiment, the positions of the light shading materials 33 are detected on the inspection screen. In contrast, in the second embodiment, the positions of the light shielding materials 33 are detected by a position sensor 34 arranged in the spatial filter 29, and the detected data are feed backed to the fluid supply mechanism by the control unit. The fluid used in the second embodiment may include any of incompressible fluids (for example, oil or water) and compressible fluids (for example, air or nitrogen), since the positions of the light shading materials 33 may be controlled with high accuracy by the control unit.

In the second embodiment, the same effects as in the first embodiment may be also achieved.

[Third Embodiment]

Figure 10A:
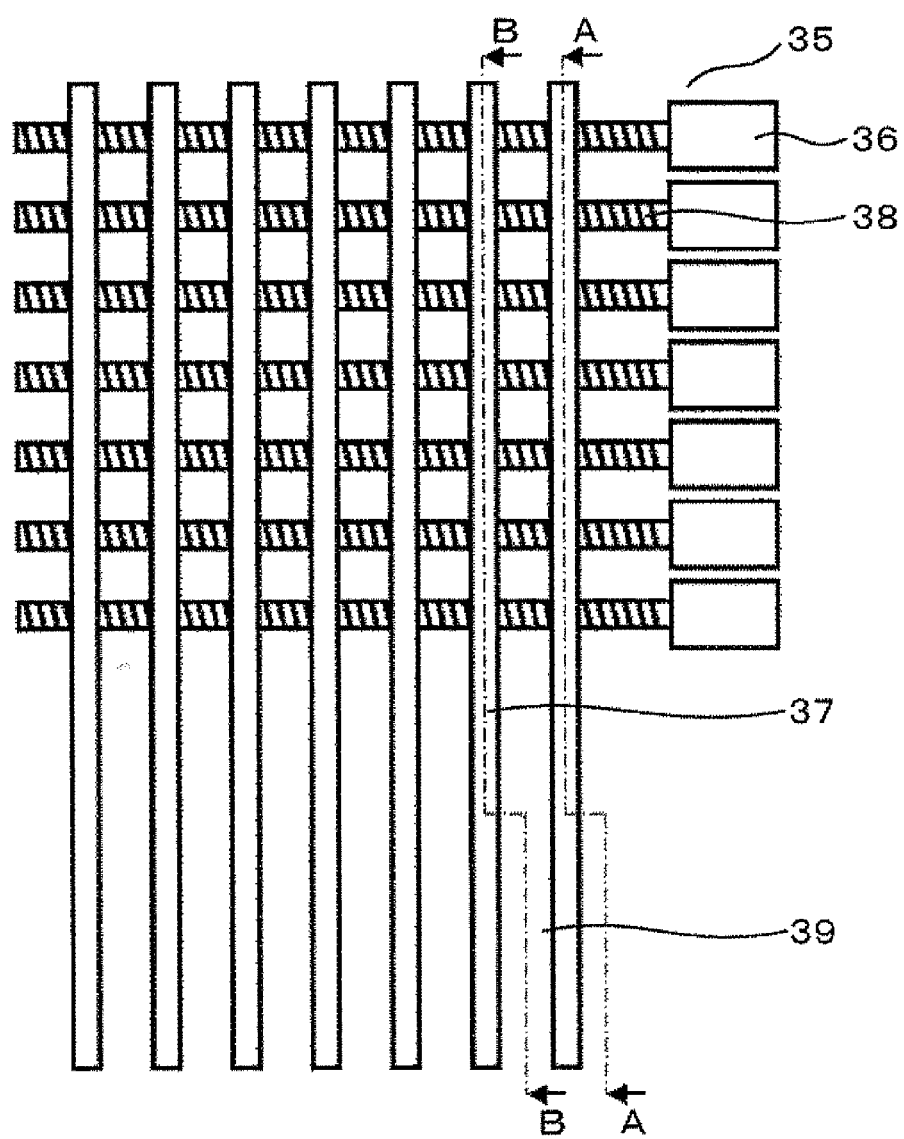
FIGS. 10A and 10B are explanatory diagrams showing a spatial filter in the third embodiment of the present invention.
Figure 10B:
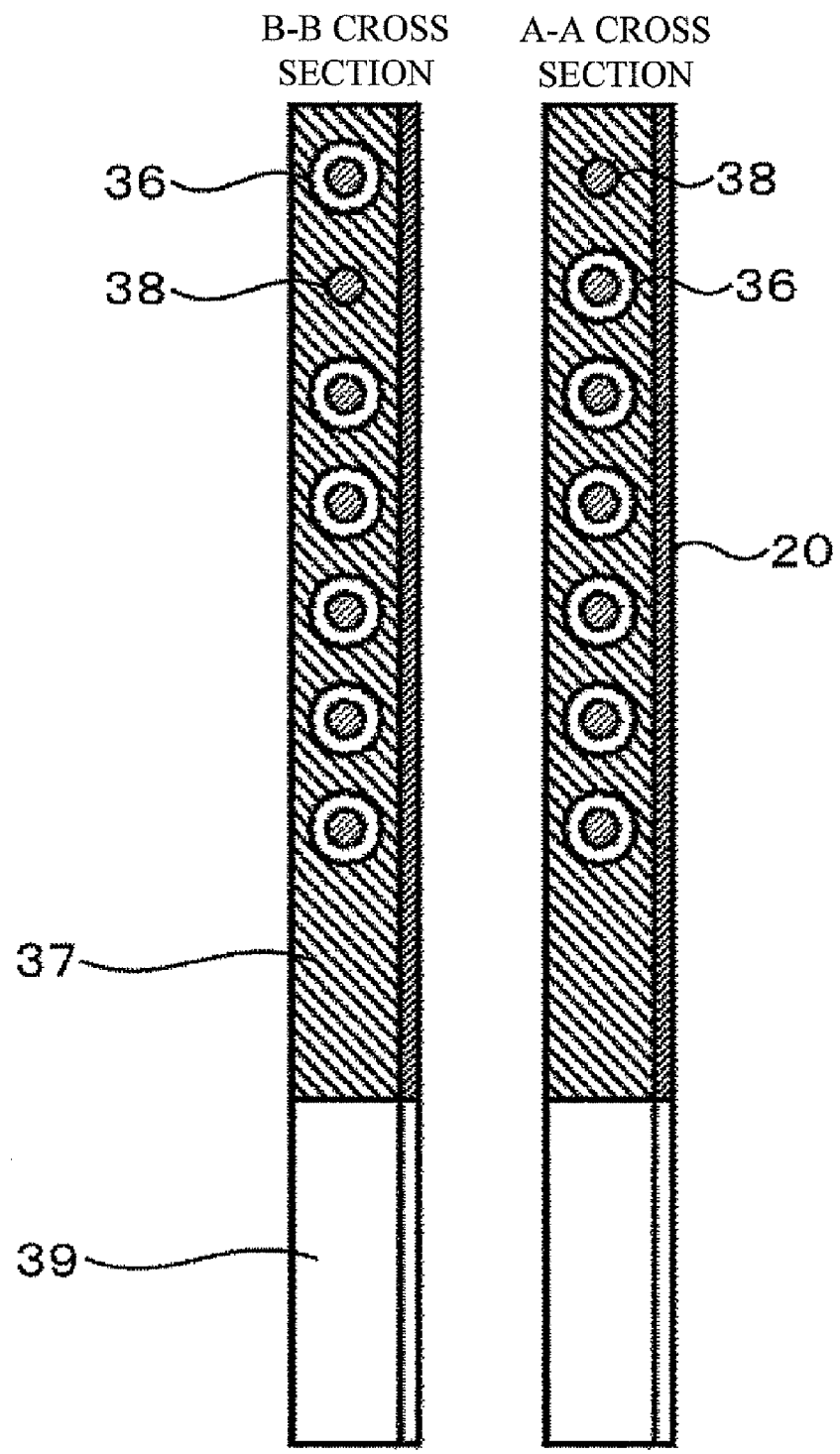

Referring to FIGS. 10A and 10B, will be explained the third embodiment of the present invention. FIG. 10A shows a top view of a spatial filter 35 and FIG. 10B shows a cross-sectional view of the spatial filter 35.

When the spatial filter 35 in the third embodiment is compared to the spatial filter 17 in the first embodiment, there are differences that screw materials 36 are arranged in the spatial filter 35 instead of the piezoelectric elements 19. Internal threads 38 are formed through the light shading material 37 and the light shading material 37 are connected with the screw material 36. Herein, the place where the light shading material 37 is connected with the screw material 36 is only one portion in each light shading material 37. Thus, the respective light shading materials 37 are independently moved, whereby the respective light shading intervals 39 may be independently controlled.

Figure 10C:
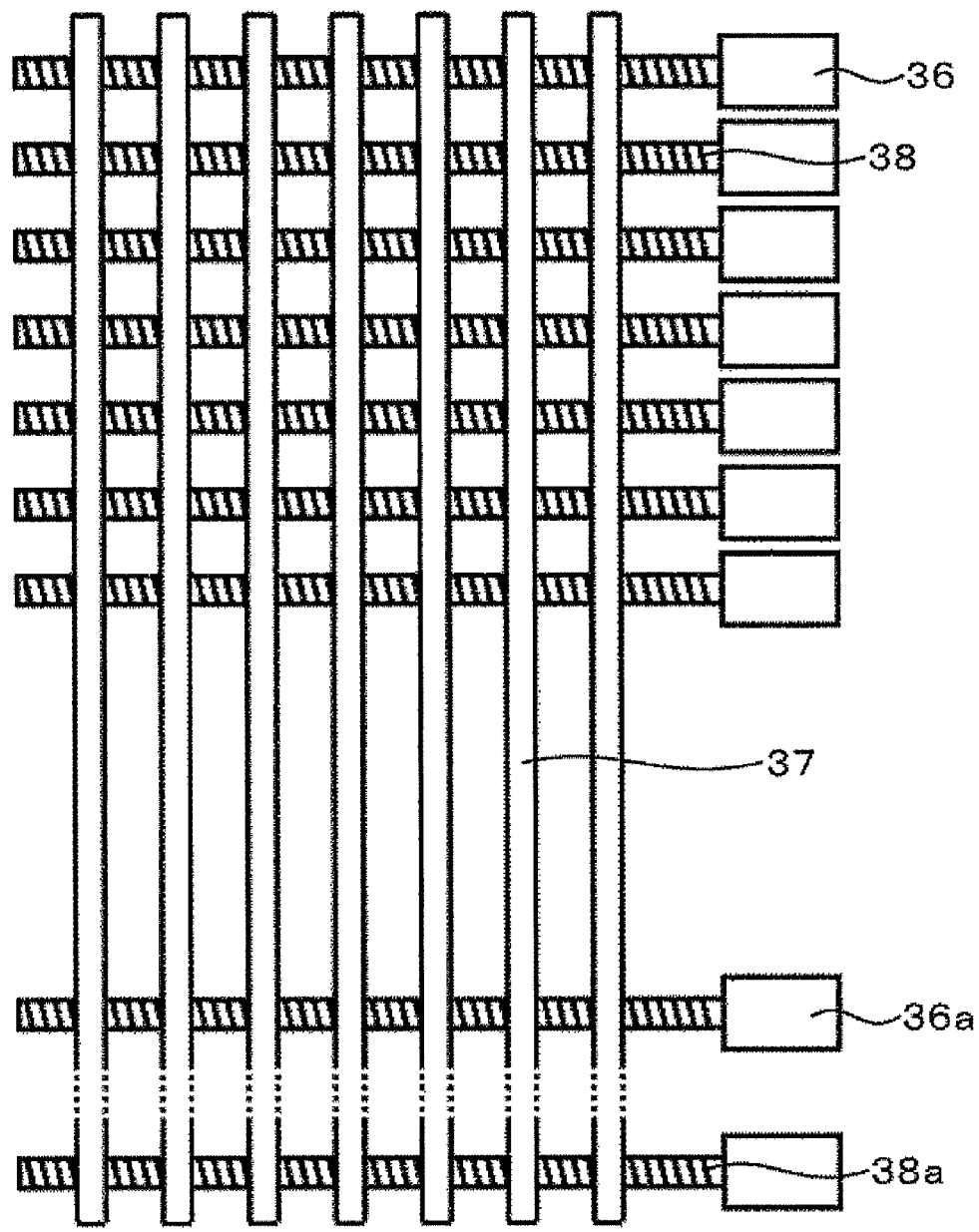
FIG. 10C is an explanatory diagram showing a case in changing an angle of the light shading material by modulating rotations of the screws.

As shown in FIG. 10C, if the screw mechanism is connected with thread holes at both sides of the light shading material 37, and the screw at one side is rotated through the thread hole once and the screw at the other side is rotated through the thread hole twice. This rotational difference in the screws connected with both thread holes of the light shading material 37 enables the light shading material 37 to be arranged with an inclining angle same as in the first embodiment.

In the present embodiment, the same effect as in the first embodiment may be also achieved.

Further, in the present embodiment, the light shading material 18 is not mutually inserted between the piezoelectric elements 19 each other, which allows the moving range of the light shading material 37 to be increased, resulting in the increase in the modification range of the light shading interval 39. Therefore, in the third embodiment, the contamination inspection device may correspond to various light shading patterns by just arranging one unit of the spatial filter 35 in the contamination inspection device.

[Fourth Embodiment]

Figure 11A:
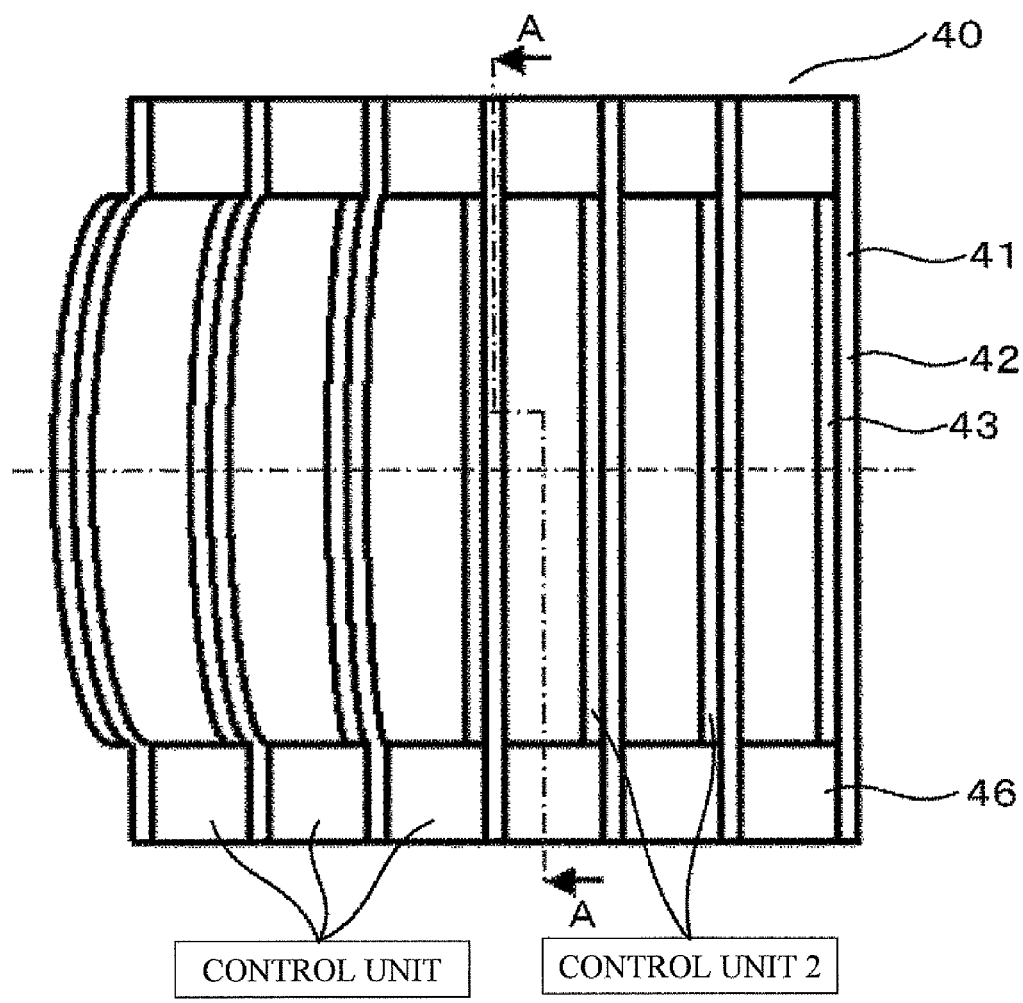
FIGS. 11A and 11B are explanatory diagrams of a spatial filter in the fourth embodiment of the present invention.
Figure 11B:
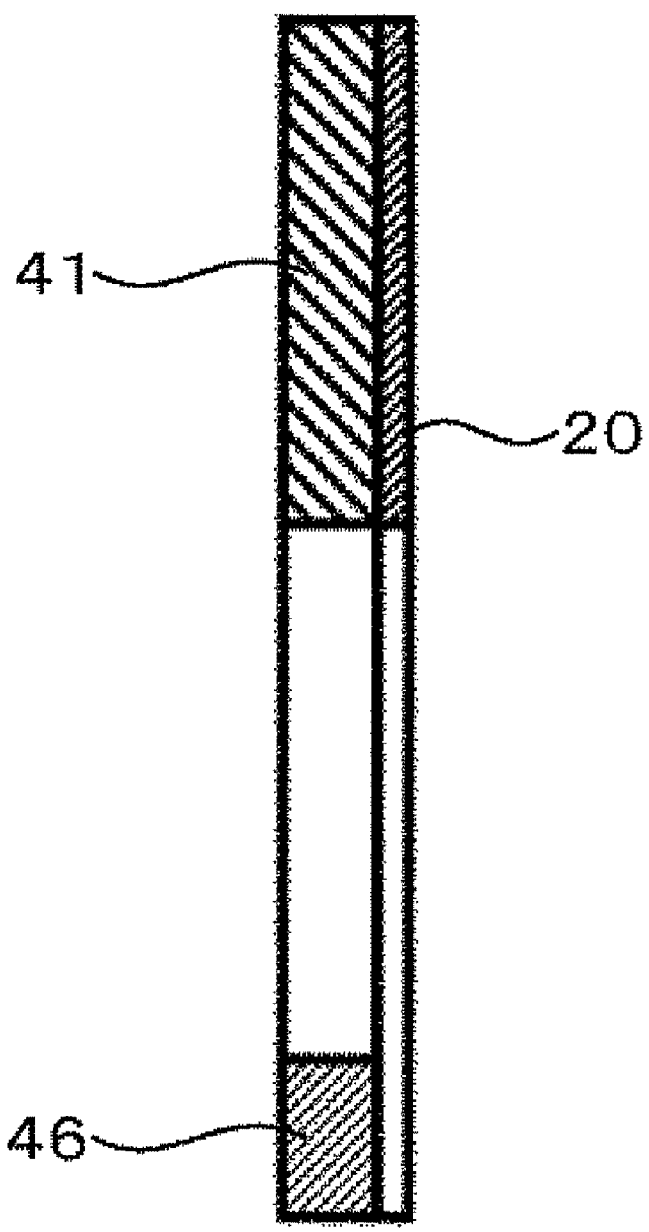

Referring to FIGS. 11A and 11B, will be explained the fourth embodiment of the present invention. FIG. 11A shows a top view of a spatial filter 40, and FIG. 11B shows a cross-sectional view of the spatial filter 40.

When the spatial filter 40 in the fourth embodiment is compared to the spatial filter 17 in the first embodiment, there is a difference that a light shading material 41 which is made by pasting rods or rod materials together, made of at least two different materials, is utilized in the fourth embodiment. In the fourth embodiment, utilized is the light shading material 41 which is made by pasting a plastic 42 on a light shading material with piezoelectric element 43. Accordingly, a shape of the light shading material 41 may be changed into a curved form by applying voltage to the light shading material with piezoelectric element 43.

In the meantime, pattern distortion of diffracted lights projected on a Fourier transformation surface is caused due to a lens aberration ———. Therefore, when a conventional linear light shading material is used, a light shading material with a wide width has to be used in order to correct the pattern distortion. However, in this procedure, even a region with unnecessary light shading also turns to be shaded, resulting in the lowering of the detection accuracy. In order to solve such an inconvenience, the light shading material 41 is made to be capable of being curved corresponding to the curved shape of the pattern distortion in the fourth embodiment. This allows the detection with the high accuracy to be achieved because it is not necessary to widen the width of the light shading material.

The light shading material 41 turns to have a curved shape protruded toward the outside as shown in FIG. 11A by applying positive voltage supplied from the control unit 2. In contrast, when negative voltage is applied to the light shading material 41, the light shading material 41 turns to have a curved shape recessed toward the inside of the filter 40. Further, when no voltage is applied to the light shading material 41, the light shading material 41 has a substantially straight shape.

Figure 12A:
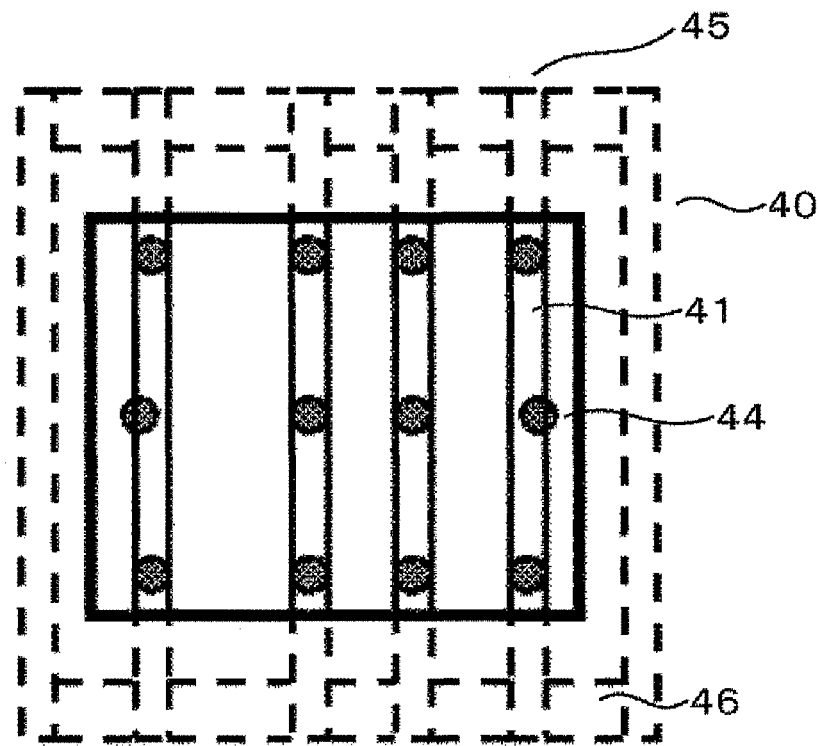
FIGS. 12A and 12B are explanatory diagrams showing the spatial filter in the fourth embodiment of the present invention.
Figure 12B:
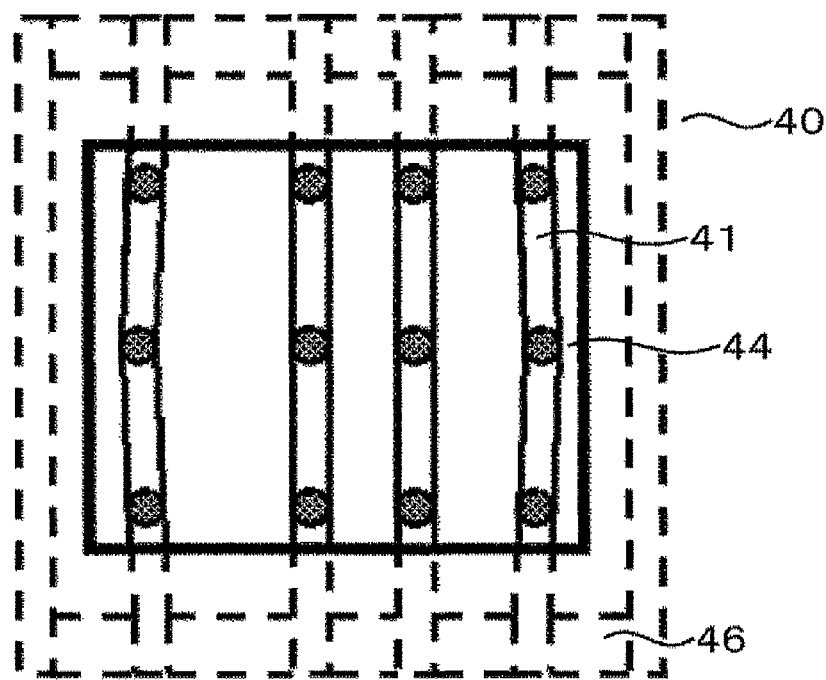

Next, will be explained the specific inspection method in the fourth embodiment. FIGS. 12A and 12B show inspection images in which diffracted lights 44 and the light shading materials 41 of the spatial filter 40 are displayed. The inspection method comprises the steps of: first displaying the diffracted lights 44 projected on the Fourier transformation surface on the inspection screen 45; secondly displaying the spatial filter 40 on the inspection screen 45 (see FIG. 12A); and thirdly having the light shading materials 41 curved by applying voltage to the light shading material with piezoelectric element 43 as corresponding to the curved shape of the pattern distortion of the diffracted lights 44 projected on the Fourier transformation pattern (see FIG. 12B).

As mentioned above, the same effects as in the first embodiment, or the superior effects thereto may be achieved.

Note the light shading material 41 is turns to be curved toward the outside of the spatial filter 40 in the present embodiment. In contrast, the light shading material 41 may be curved toward the inside of the spatial filter 40 by reversing the positive voltage applied to the light shading material with piezoelectric element 43 into the negative voltage applied thereto. Further, it should be noted that the construction in which the light shading material with piezoelectric element 43 is pasted on the light shading material 41 is not limited to the construction shown in FIGS. 11A and 11B. That is, various modifications of the construction may be performed in the present invention.

Moreover, similarly to the first embodiment, the light shading materials 41 maybe arranged at uneven intervals or with having inclining angles (or arranged at the uneven intervals with having inclining angles) through respectively controlling the voltage applied to the piezoelectric elements 46.

[Fifth Embodiment]

Figure 13A:
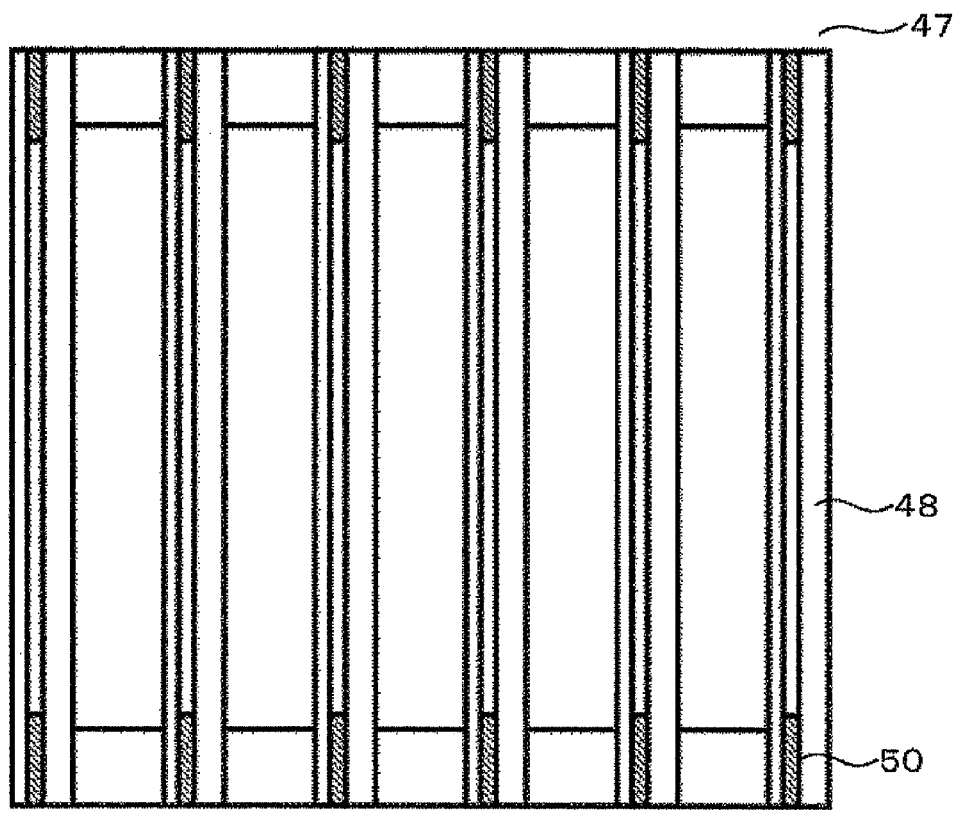
FIGS. 13A and 13B are explanatory diagrams of a spatial filter in the fifth embodiment of the present invention.
Figure 13B:
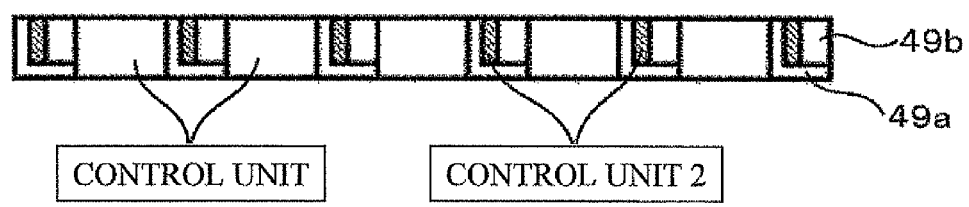

Next, will be explained the fifth embodiment of the present invention. FIG. 13A shows a top view and FIG. 13B shows a side view of the spatial filter 47. When the spatial filter 47 is compared to the spatial filter 17 shown in FIGS. 1A and 1B, there is a difference that a light shading material with piezoelectric element 50 is held between two rod materials (49a and 49b) which are to be a light shading material 48.

Figure 14A:
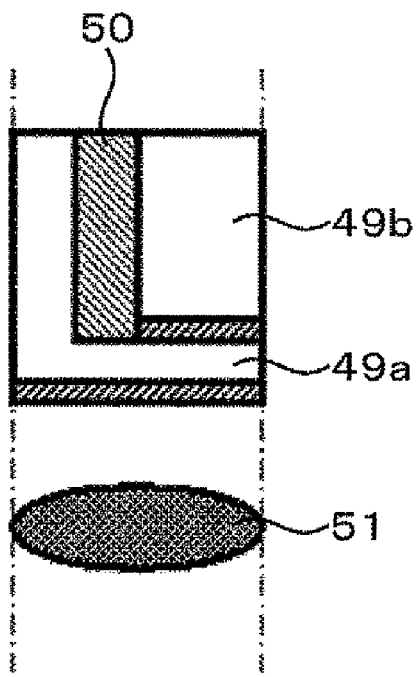
FIGS. 14A and 14B are explanatory diagrams showing a method for shading the diffracted lights by the spatial filter in the fifth embodiment of the present invention.
Figure 14B:
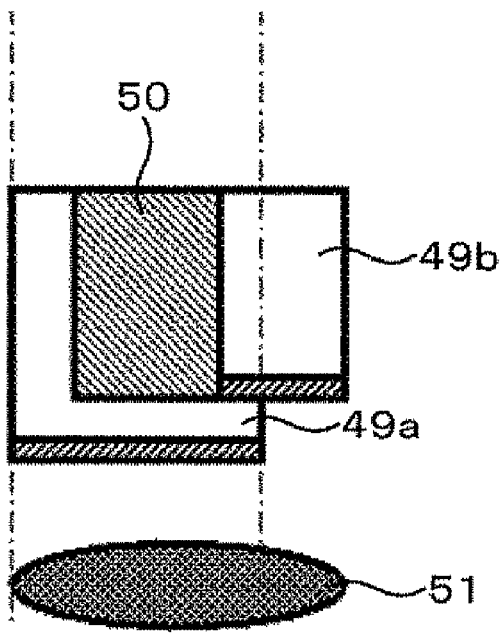

FIGS. 14A and 14B show light shading images in the fifth embodiment. More specifically, FIG. 14A shows a small size of the diffracted light 51 projected on the Fourier transformation surface, while FIG. 14B shows a large size of the diffracted light 51 projected on the Fourier transformation surface. In the fifth embodiment, the width of the light shading material 48 is configured capable of being expanded or contracted, by expanding or contracting the light shading material with piezoelectric element 50. This construction enables the width of the light shading material to be changed corresponding to a size of the diffracted light 51 projected on the Fourier transformation surface, resulting in the excellent light shading performance with high accuracy.

As mentioned hereinbefore, the same effects as in the first embodiment, or the superior effects thereto may be achieved.

[Sixth Embodiment]

Figure 15A:
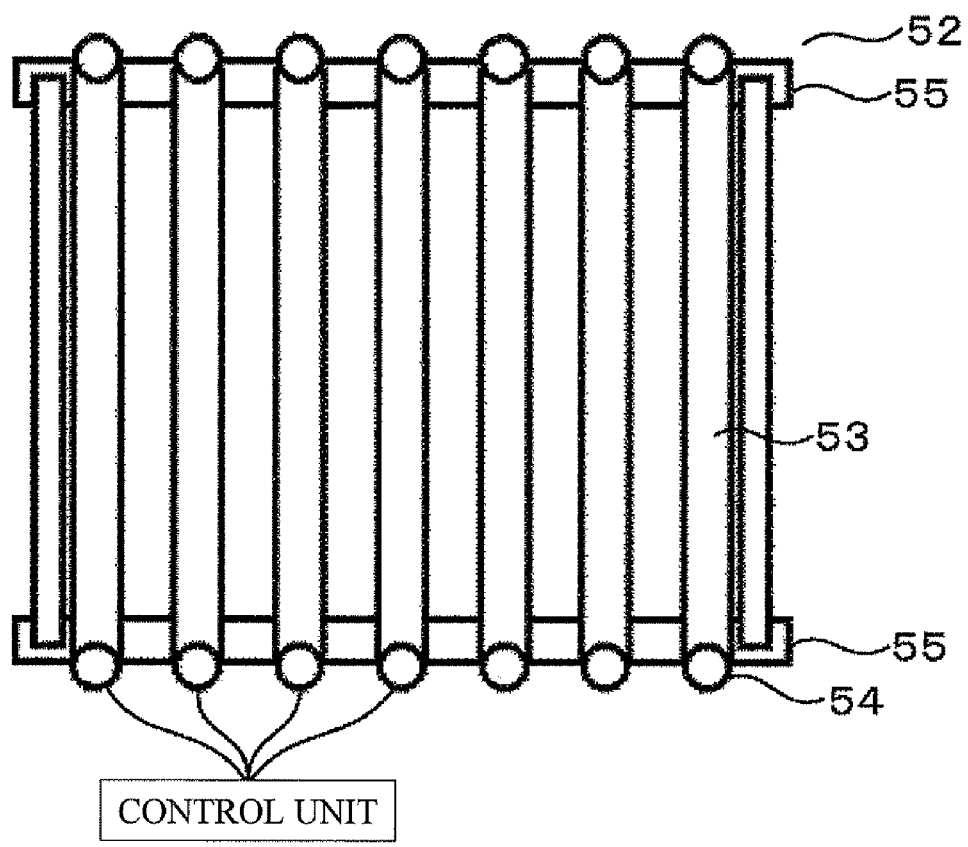
FIGS. 15A and 15B are explanatory diagrams showing a spatial filter in the sixth embodiment of the present invention.
Figure 15B:
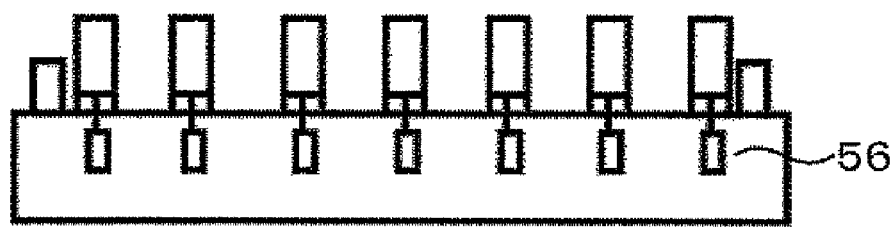

Next, referring to FIGS. 15A and 15B, will be explained the sixth embodiment of the present invention. FIG. 15A shows a top view of a spatial filter 52, and FIG. 15B shows a cross-sectional view of the spatial filter 52.

When the spatial filter 52 in the sixth embodiment is compared to the spatial filter 17 in the first embodiment, there is a difference that a motor 54 is used as a mechanism for moving the light shading material 18, instead of the piezoelectric element 19 as a moving mechanism.

Here, the motors 54 are attached at both ends of the light shading material 53 in a downward direction, and a roller 56 is attached at a forward position of the motor 54. Herein, the roller 56 is attached to a guide 55 with no gap. This allows the light shading materials 53 to be moved in parallel, resulting in the achievement of the same effects as in the first embodiment.

Regarding a type of the motor 54, an AC motor, a DC motor, together with an ultrasonic motor may be used to achieve the same effects.

Further, in the sixth embodiment, the spatial filter 52 is not configured such that the light shading material 18 and the piezoelectric element 19 are not mutually put in one another. Accordingly, this construction allows the same effects as in the third embodiment to be achieved.

[Seventh Embodiment]

Figure 16A:
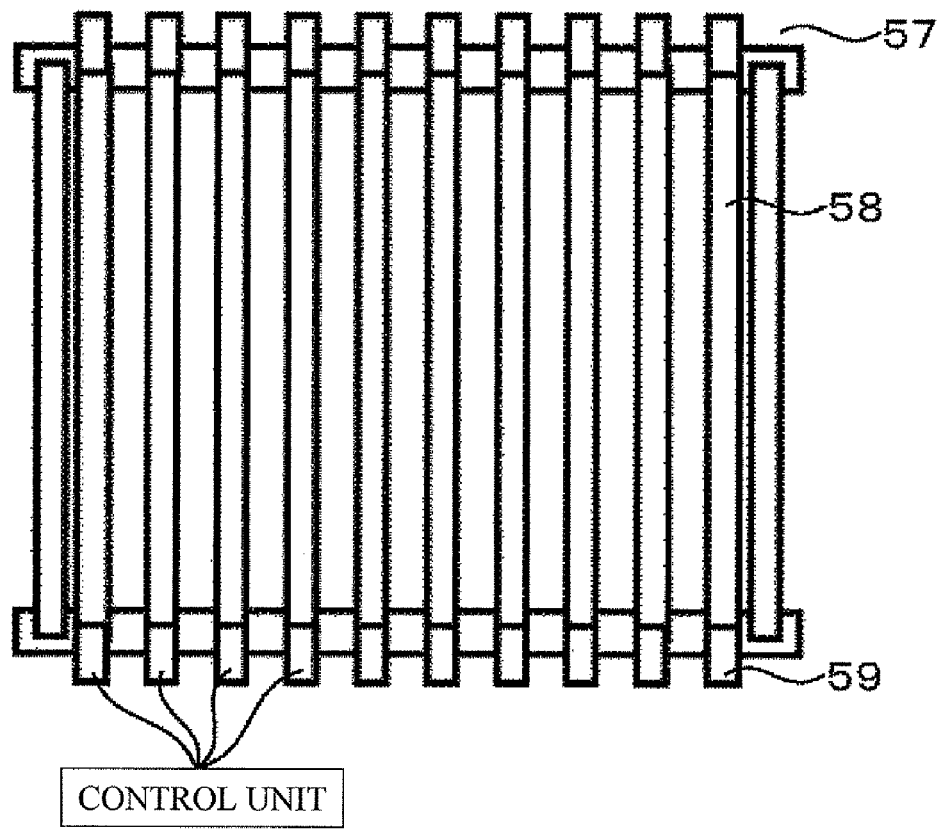
FIGS. 16A and 16B are explanatory diagrams showing a spatial filter in the seventh embodiment of the present invention.
Figure 16B:
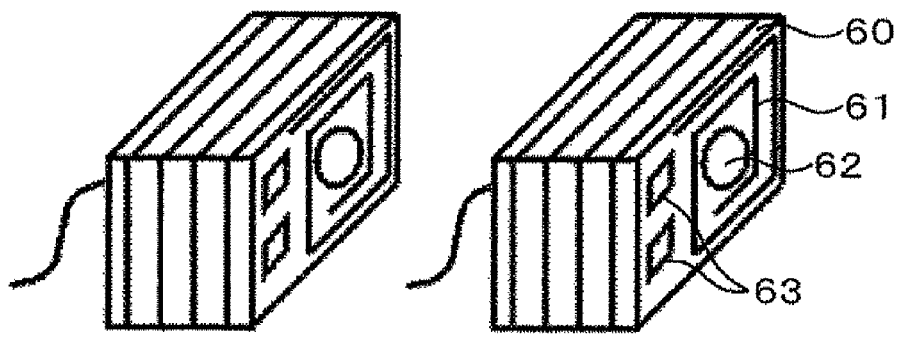

Next, referring to FIGS. 16A and 16B, will be explained the seventh embodiment of the present invention. FIG. 16A shows a top view of a spatial filter 57, and FIG. 16B shows a magnified view of a part of a magnet unit 59.

When the spatial filter 57 in the seventh embodiment is compared to the spatial filter 52 in the sixth embodiment, there is a difference that the motor 54 for moving the light shading material is replaced with a magnet unit 59.

The magnet unit 59 attached to both ends of the light shading material 58 enables the light shading material 58 to be moved by repulsive force or attractive force of the magnetic force. As shown in FIG. 16B, the magnet unit 59 applies a principle of an electromagnet and is produced by the steps of: forming a wiring pattern 61 in place of coils on a multi-layered substrate 60; inserting an iron core 62 for focusing a magnetic field; and making sensors 63 for measuring an interval between the light shading materials 58 adjacent each other and controlling the light shading materials 58, thereby to assemble the abovementioned parts into one unit.

Accordingly, the above mentioned construction in the seventh embodiment allows the same effects as in the sixth embodiment to be achieved.

As mentioned hereinbefore, the first to the seventh embodiments have been explained. Note the same effects as in the first embodiment may be also achieved by a combination of the two or more embodiments described above (for example, a combination of the fourth embodiment and the fifth embodiment).

DESCRIPTION OF REFERENCE NUMERALS

1 Laser
2 Wafer
3 Stage
4 Detection lens
5, 17, 29, 35, 40, 47, 52, 57 Spatial filter
6 Condensing lens system
7 Detector
8 Spatial filter control unit
9 Spatial filter controlling cable
10 Laser beam
11 Half mirror
12 CCD camera
13 Keyboard
14 Monitor
15 Control personal computer
16 Control and data collecting cable
18, 23, 33, 37, 41, 48, 53, 58, 101, 102, 103, 104, 105 Light shading material
19, 46, 106, 107, 108, 109, 110, 111, 112, 113 Piezoelectric element
20 Anti-reflection material
21, 27, 28, 32, 39 Light shading material interval
22a Picture element (OFF)
22b Picture element (ON)
24 Coil spring
25, 45 Inspection screen
26, 44 Diffracted light projected on the Fourier transformation surface
30 Elastic materials driven by fluid
31 Tube
34 Position sensor
36, 36a Screw material
38, 38a Internal threads
42 Plastic
43, 50 light shading material with piezoelectric element
49a, 49b Rod material
54 Motor
55 Guide
56 Roller
59 Magnet unit
60 Multilayered substrate
61 Wiring pattern
62 Iron core
63 Sensor
250, 251 Modulation screen
252 Modulation start button
253 Positional data selection button
254 Positional data acquiring button
255 Positional data input field
S1-S9 Steps

The invention claimed is:

1. An inspection device comprising:
an irradiation optical system for irradiating light on an inspection target substrate;
a detecting optical system for detecting light from the inspection target substrate; and
a spatial filter for shading diffracted light from the inspection target substrate, wherein the spatial filter includes:
light shading members; and
a control member for independently moving the plurality of light shading members in an orthogonal direction relative to an optical axis of the detecting optical system independently from each other to control arrangement of the slight shading members and form a light shading pattern.

2. The inspection device as described in claim 1, further comprisisng a control unit configured to control at least one parameter selected from voltage applied to the control member, a magnetic field or a flow rate of fluid.

3. The inspection device as described in claim 1, wherein the control member is comprised of a piezoelectric member.

4. The inspection device as described in claim 1, wherein the control member is comprised of an elastic material.

5. The inspection device as described in claim 1, wherein the control member comprises at least two rotational members connected with the light shading members.

6. The inspection device as described in claim 1, wherein each of the light shading members is constituted of at least two members,
one of the at least two members is a piezoelectric member, and
a voltage control unit for applying a voltage to the piezoelectric member.

7. The inspection device as described in claim 1, wherein the light shading members are rod-shaped, and wherein the control member is comprised of motors respectively arranged at both ends of each of the light shading members.

8. The inspection device as described in claim 1, wherein the control member is comprised of a magnetic substance.

9. The inspection device as described in claim 1, wherein neighboring light shading members are not arranged at a constant interval.

10. The inspection device as described in claim 1, wherein the control member changes at least one parameter selected from a shape of the light shading patter, an angle of a light shading member relative to a neighboring light shading member and an interval of the light shading members.

11. A method for inspecting a substrate, comprising:
irradiating light on the substrate;
moving light shading members in an orthogonal direction relative to an optical axis of a detection system independently from each other to control arrangement of the light shading members and form a light shading pattern, thereby to shade diffracted light in the light from the substrate and acquire an image; and
detecting a defect of the substrate based on the image.

12. The method for inspecting a substrate as described in claim 11, wherein neighboring light shading members are not arranged at a constant interval.

13. The method for inspecting a substrate as described in claim 11, wherein the control member changes at least one of parameters parameter selected from a shape of the light shading patter, an angle of a light shading member relative to a neighboring light shading member and an interval of the light shading members.

14. A spatial filter comprising:
a plurality of light shading members; and
a control member configured to independently move the plurality of light shading members in an orthogonal direction relative to an optical axis of a detection system independently from each other to control arrangement of the light shading members and form a light shading pattern.

15. The spatial filter according to claim 14, wherein the control member is comprised of a piezoelectric member.

16. The spatial filter according to claim 15, wherein neighboring light shading members are not arranged at a constant interval.

17. The spatial filter according to claim 14, wherein the control member is comprised of an elastic material.

18. The spatial filer according to claim 14, wherein the control member comprises at least two rotational members connected with the light shading members.

19. The spatial filter according to claim 14, wherein the control member is comprised of a magnetic substance.

* * * * *